(12) United States Patent
Fukuda et al.

(10) Patent No.: US 8,008,089 B2
(45) Date of Patent: Aug. 30, 2011

(54) METHOD AND SYSTEM FOR CHECKING MEASUREMENT RESULT

(75) Inventors: Masakazu Fukuda, Kobe (JP); Yutaka Ikeda, Kakogawa (JP); Hiromi Onomichi, Kobe (JP)

(73) Assignee: Sysmex Corporation, Kobe (JP)

( * ) Notice: Subject to any disclaimer, the term of this patent is extended or adjusted under 35 U.S.C. 154(b) by 737 days.

(21) Appl. No.: 11/238,896

(22) Filed: Sep. 29, 2005

(65) Prior Publication Data
US 2007/0072301 A1 Mar. 29, 2007

(30) Foreign Application Priority Data

Sep. 29, 2004 (JP) ................. 2004-284851

(51) Int. Cl.
*G01N 25/08* (2006.01)
*G01N 27/00* (2006.01)
*G01N 21/00* (2006.01)

(52) U.S. Cl. ............... 436/150; 436/8; 436/10; 436/12; 436/50; 436/149; 422/82.02; 356/337; 702/19

(58) Field of Classification Search ............... 436/8–19, 436/149; 702/19, 22, 27, 28, 30, 32; 356/73; 422/63
See application file for complete search history.

(56) References Cited

U.S. PATENT DOCUMENTS

| | | | |
|---|---|---|---|
| 5,038,109 A | 8/1991 | Goble et al. | |
| 5,325,168 A | 6/1994 | Nakamoto et al. | |
| 5,631,163 A * | 5/1997 | Pugia et al. | 436/2 |
| 5,757,475 A * | 5/1998 | Katayama et al. | 356/73 |
| 5,851,487 A | 12/1998 | Katayama et al. | |
| 6,021,339 A * | 2/2000 | Saito et al. | 600/345 |
| 6,183,697 B1 * | 2/2001 | Tanaka et al. | 422/82.05 |
| 2006/0073606 A1 * | 4/2006 | Fukuda | 436/155 |
| 2006/0253064 A1 * | 11/2006 | Gelfand et al. | 604/31 |

FOREIGN PATENT DOCUMENTS

| | | | |
|---|---|---|---|
| JP | H02-027262 | | 1/1990 |
| JP | 03009262 A | * | 1/1991 |
| JP | 5-322885 | * | 12/1993 |

OTHER PUBLICATIONS

Machine Translation of Japan application, JP 5-322885, Dec. 7, 1993, 22 pages.*

* cited by examiner

*Primary Examiner* — Jill Warden
*Assistant Examiner* — Dean Kwak
(74) *Attorney, Agent, or Firm* — Brinks Hofer Gilson & Lione

(57) ABSTRACT

A system for checking measurement results is provided with a urine qualitative analyzer for measuring the specific gravity of a urine, urinary particle analyzer for measuring urine conductivity, and a computer. The urine specific gravity measured by the urine qualitative analyzer, and the urine conductivity measured by the urinary particle analyzer are respectively transmitted to the computer. The correlative relationship between urine specific gravity and urine conductivity is stored in the memory of the computer, and the computer determines whether or not the received urine specific gravity and conductivity match the correlative relationship, and this determination result is output.

12 Claims, 18 Drawing Sheets

METHOD AND SYSTEM FOR CHECKING MEASUREMENT RESULT

This application claims priority under 35 U.S.C. §119 to Japanese Patent Application No. 2004-284851 filed Sep. 29, 2004, the entire content of which is hereby incorporated by reference.

FIELD OF INVENTION

The present invention relates to a method for checking measurement results in which urine analysis measurement results are checked, system for checking measurement results using this method, apparatus for checking measurement results, and computer-readable storage medium stored a computer program for having a computer function as the apparatus for checking measurement results.

BACKGROUND

Urine qualitative analyzers and urinary particle analyzers are widely known urine analyzers used in urine testing. Urine qualitative analyzers generally automatically take a test paper on which reaction test pieces are adhered for each measurement item and immerse the test paper in a collected urine sample for a predetermined time, then compare the colors of the test pieces to standard determination colors to obtain negative and positive results ((−), (±), (+)) for each item (for example, refer to Japanese Laid-Open Patent Publication No. 2-27262). Urinary particle analyzers automatically classify and count the urinary particles (for example, refer to U.S. Pat. No. 5,325,168).

These urine qualitative analyzers and urinary particle analyzers may have lower measurement accuracy due to the influence of measurement volume and impurities contained in the urine. Furthermore, a measurement result checking device has been proposed for mutually checking the highly correlated measurement results of urine qualitative analyzers and measurement results of urinary particle analyzers, and evaluating the reliability of the measurement results (refer to U.S. Pat. No. 5,851,487).

Urine specific gravity, which is one measurement item of urine qualitative analyzers, is known to have a high correlation with urine conductivity (for example, refer to U.S. Pat. No. 5,038,109).

The previously disclosed checking device, however, is not configured to check measurement results of specific gravity, and has had low reliability for specific gravity measurement results.

BRIEF SUMMARY

The scope of the present invention is defined solely by the appended claims, and is not affected to any degree by the statements within this summary.

In view of the aforesaid information, an object of the present invention is to provide a method for checking measurement results which is capable of evaluating the reliability of the measurement results, system for checking measurement results using this method, apparatus for checking measurement results, and computer-readable storage medium stored a computer program for having a computer function as the apparatus for checking measurement results.

A further object of the present invention is to provide a method for checking measurement results that is capable of checking urine specific gravity measurement results and urine conductivity measurement results and evaluating the reliability of the measurement results, system for checking measurement results using this method, apparatus for checking measurement results, and computer-readable storage medium stored a computer program for having a computer function as the apparatus for checking measurement results.

The first aspect of the present invention relates to a method for checking measurement results comprising a specific gravity measuring step for measuring a specific gravity of a urine, a conductivity measuring step for measuring a conductivity of the urine, a determination step for determining reliability of at least one of the measurement results of the specific gravity and the conductivity based on a predetermined correlative relationship of urine specific gravity and urine conductivity, and a display step for displaying the determination result of the determination step.

The second aspect of the present invention relates to a system for checking measurement results comprising a first analyzer for measuring a specific gravity of a urine, a second analyzer for measuring a conductivity of the urine, a determination means for determining reliability of at least one of the measurement results of the specific gravity measured by the first analyzer and the conductivity measured by the second analyzer based on a predetermined correlative relationship of urine specific gravity and urine conductivity, and an output means for outputting the determination result of the determination means.

The third aspect of the present invention relates to a system for checking measurement results comprising a conductivity measuring unit for measuring conductivity of a urine, a sugar measuring unit for measuring a sugar concentration of urine, a comparison means for comparing the sugar concentration measured by the sugar concentration measuring unit and a predetermined threshold value, and an output means for outputting what indicates low reliability of the measured urine conductivity when comparison result of the comparison means indicates the measured sugar concentration exceeds the threshold value.

The fourth aspect of the present invention relates to an apparatus for checking measurement results comprising a specific gravity obtaining means for obtaining a measurement result of a specific gravity of a urine, a conductivity obtaining means for obtaining a measurement result of a conductivity of the urine, a determination means for determining reliability of at least one of the measurement results of the specific gravity obtained by the specific gravity obtaining means and the conductivity obtained by the conductivity obtaining means based on a predetermined correlative relationship of urine specific gravity and urine conductivity, and an output means for outputting the determination result of the determination means.

The fifth aspect of the present invention relates to a computer readable storage medium stored a computer program for checking the measurement results of a urine using a computer, wherein the computer program comprises a first obtaining means for obtaining a measurement result of specific gravity of a urine using the computer, a second obtaining means for obtaining a measurement result of conductivity of the urine using the computer, a determination means for determining the reliability of at least one of the measurement results of the specific gravity obtained by the first obtaining means and the conductivity obtained by the second obtaining means based on a predetermined correlative relationship of urine specific gravity and urine conductivity, and wherein the output means outputs the determination result of the determination means using the computer.

DETAILED DESCRIPTION OF THE PREFERRED EMBODIMENTS

The embodiments of the present invention are described hereinafter based on the drawings.

Figure 1:
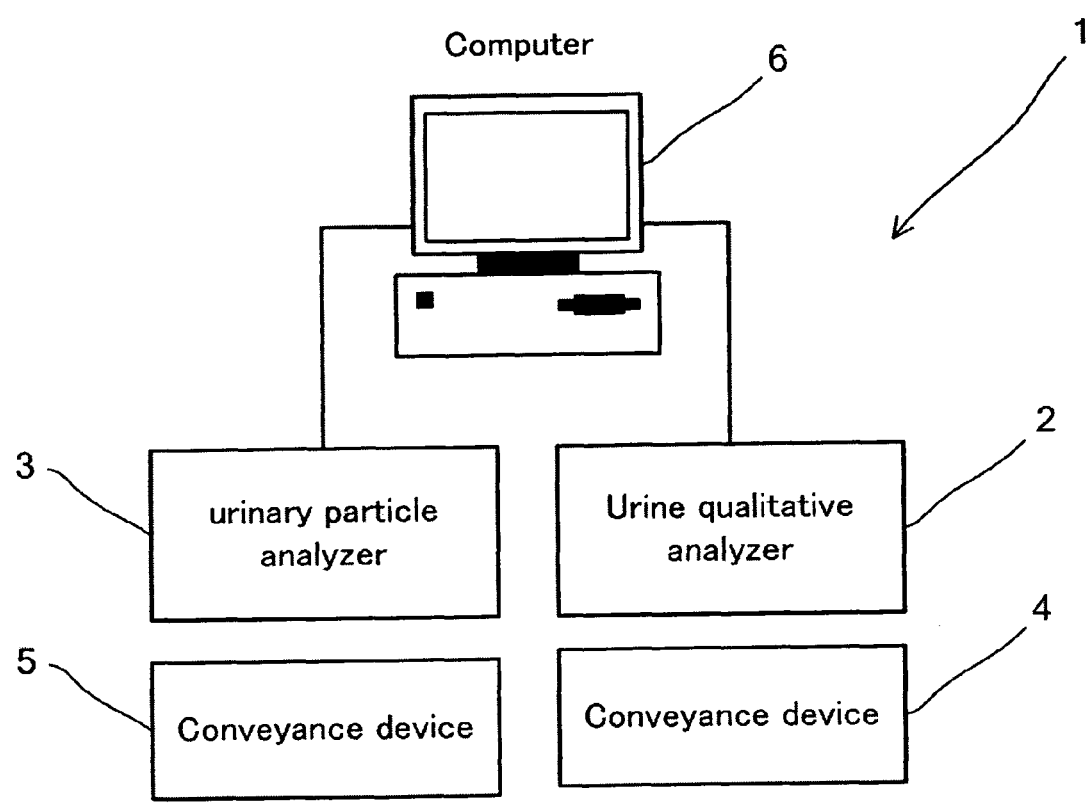
FIG. 1 is a schematic view showing the structure of the system for checking measurement results of an embodiment of the present invention.

FIG. 1 is a schematic view showing the structure of the system for checking measurement results of an embodiment of the present invention. As shown in FIG. 1, the system for checking measurement results 1 of the present embodiment is mainly configured by a urine qualitative analyzer 2, urinary particle analyzer 3, conveyance devices 4 and 5, and computer 6. The computer 6 is electrically connected to the urine qualitative analyzer 2 and urinary particle analyzer 3, and is capable of mutual data communication with the urine qualitative analyzer 2 and urinary particle analyzer 3.

Figure 2:
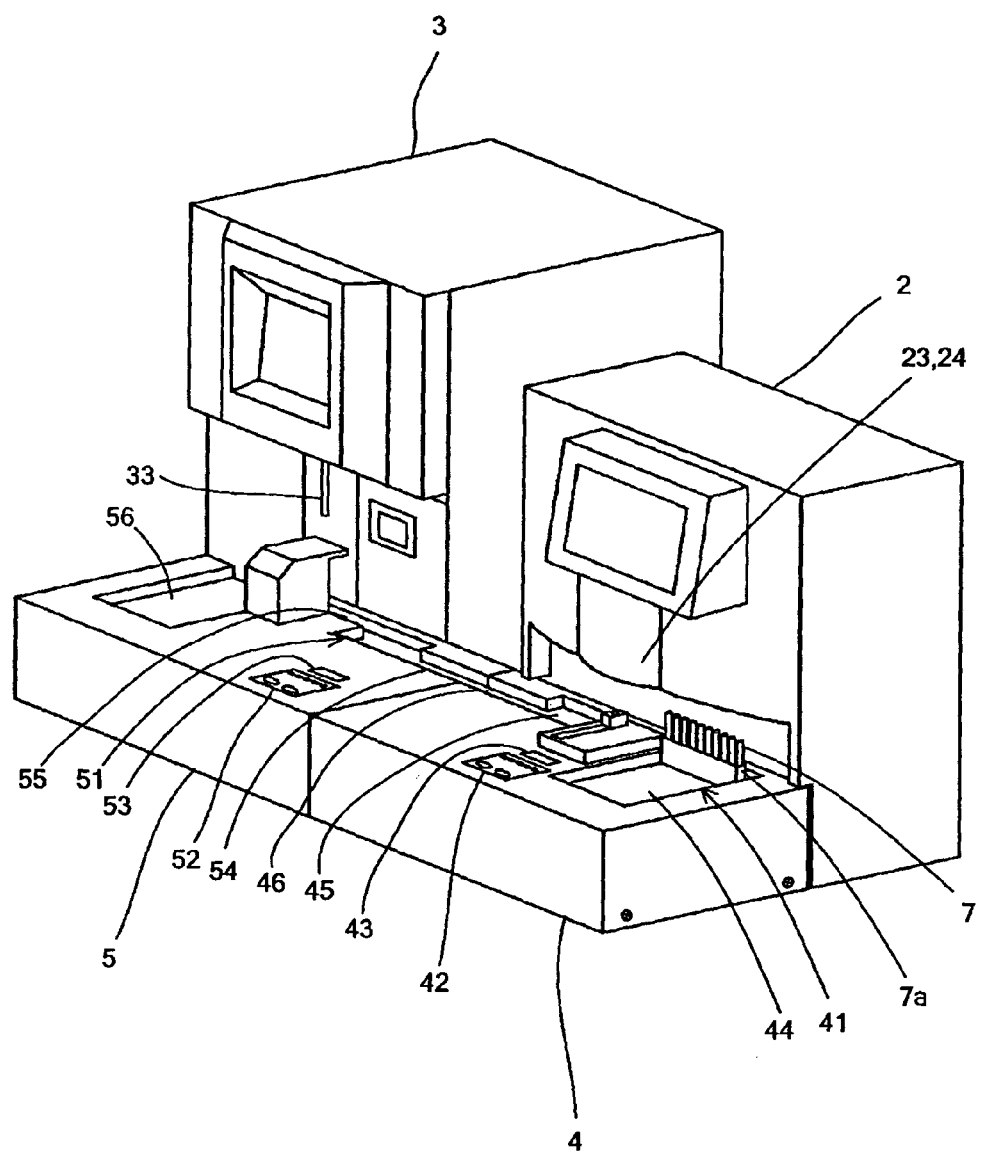
FIG. 2 is a perspective view showing part of the structure of the system for checking measurement results of the embodiment of the present invention.

FIG. 2 is a perspective view showing part of the structure of the system for checking measurement results 1 of the present embodiment. As shown in FIG. 2, the urine qualitative analyzer 2 and urinary particle analyzer 3 are disposed adjacently, and the conveyance device 4 is arranged in front of the urine qualitative analyzer 2, and the conveyance device 5 is arranged in front of the urinary particle analyzer 3. The conveyance devices 4 and 5 are mutually connected by bolts or the like, so as to be capable of continuous conveyance of a sample between the conveyance devices 4 and 5 as described later. The conveyance device 4 is configured so as to automatically supply a sample to the urine qualitative analyzer 2, and the conveyance device 5 is configured so as to automatically convey a sample received from the conveyance device 4 to the urinary particle analyzer 3.

Figure 3:
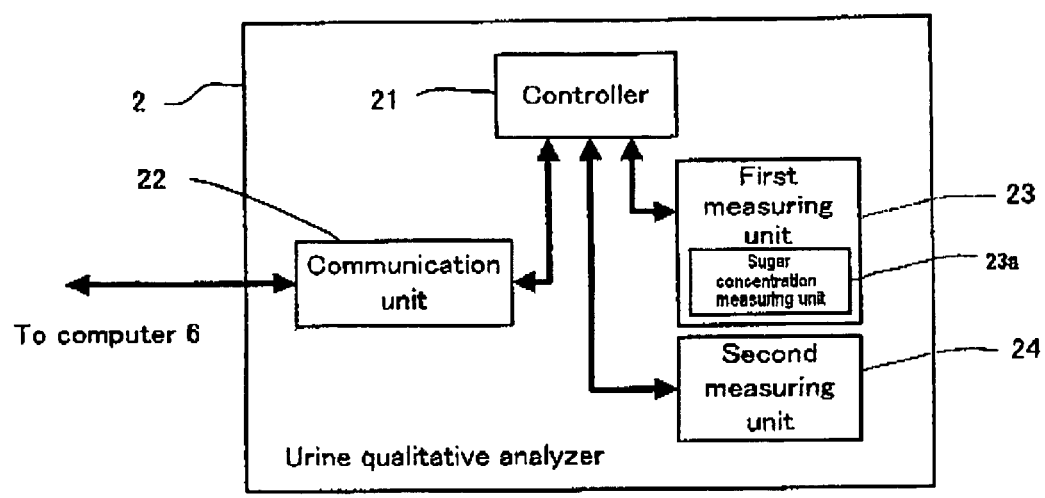
FIG. 3 is a block diagram showing the structure of the urine qualitative analyzer.

FIG. 3 is a block diagram showing the structure of the urine qualitative analyzer 2. As shown in FIG. 3, the urine qualitative analyzer 2 mainly includes a controller 21 configured by a CPU, ROM, RAM and the like, communication unit 22 for sending and receiving data to/from the computer 6, first measuring unit 23 for immersing in a supplied sample test papers corresponding to various measurement items (occult blood concentration, protein concentration, white blood cell concentration (white blood cell esterase reaction), nitrite concentration, and glucose concentration), and second measuring unit 24 for detecting the refractive index of the sample and measuring the specific gravity of the sample from this refractive index. The first measuring unit 23 includes a sugar concentration measuring unit 23a for measuring a glucose concentration of the sample. The urine qualitative analyzer 2 automatically classifies occult blood concentration, protein concentration, white blood cell concentration, nitrite concentration, and glucose concentration by the degree of color change of the test paper in the nine levels (−), (±), (2+), (3+), . . . , (7+), and transmits the respective corresponding measurement result data from the communication unit 22 to the computer 6; and transmits the measurement result data reflecting the measured value of specific gravity from the communication unit 22 to the computer 6.

Figure 4:
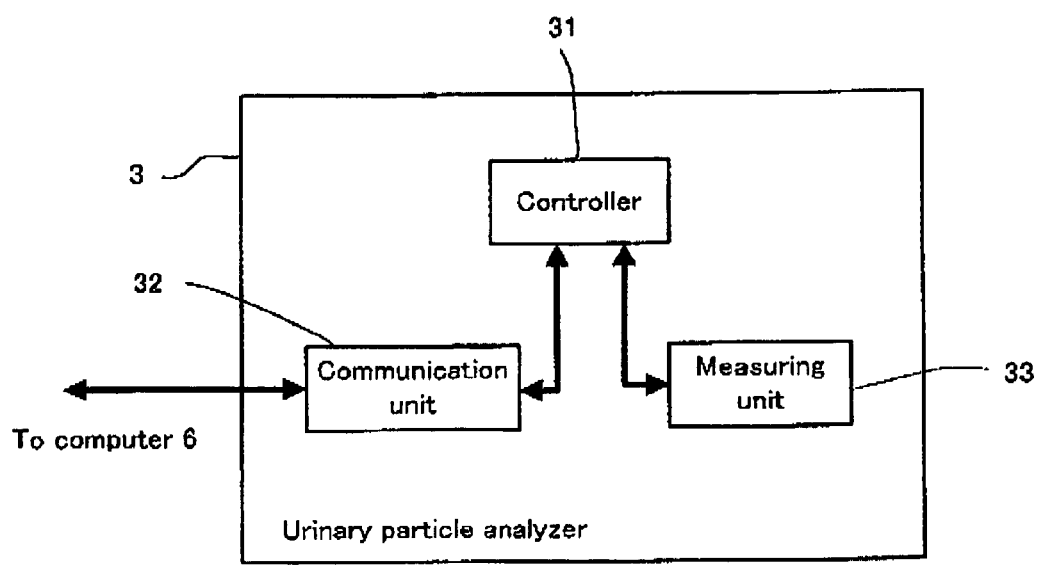
FIG. 4 is a block diagram showing the structure of the analyzer for analyzing urinary particles.

FIG. 4 is a block diagram showing the structure of the analyzer for analyzing urinary particles. As shown in FIG. 4, the urinary particle analyzer 3 mainly includes controller 31 configured by a CPU, ROM, RAM and the like, communication unit 32 for sending and receiving data to/from the computer 6, and a measuring unit 33 for obtaining measurement values for various measurement items related to particles (red blood cells, white blood cells, casts, bacteria and the like) in supplied sample urine using a flow cytometric method.

Figure 5:
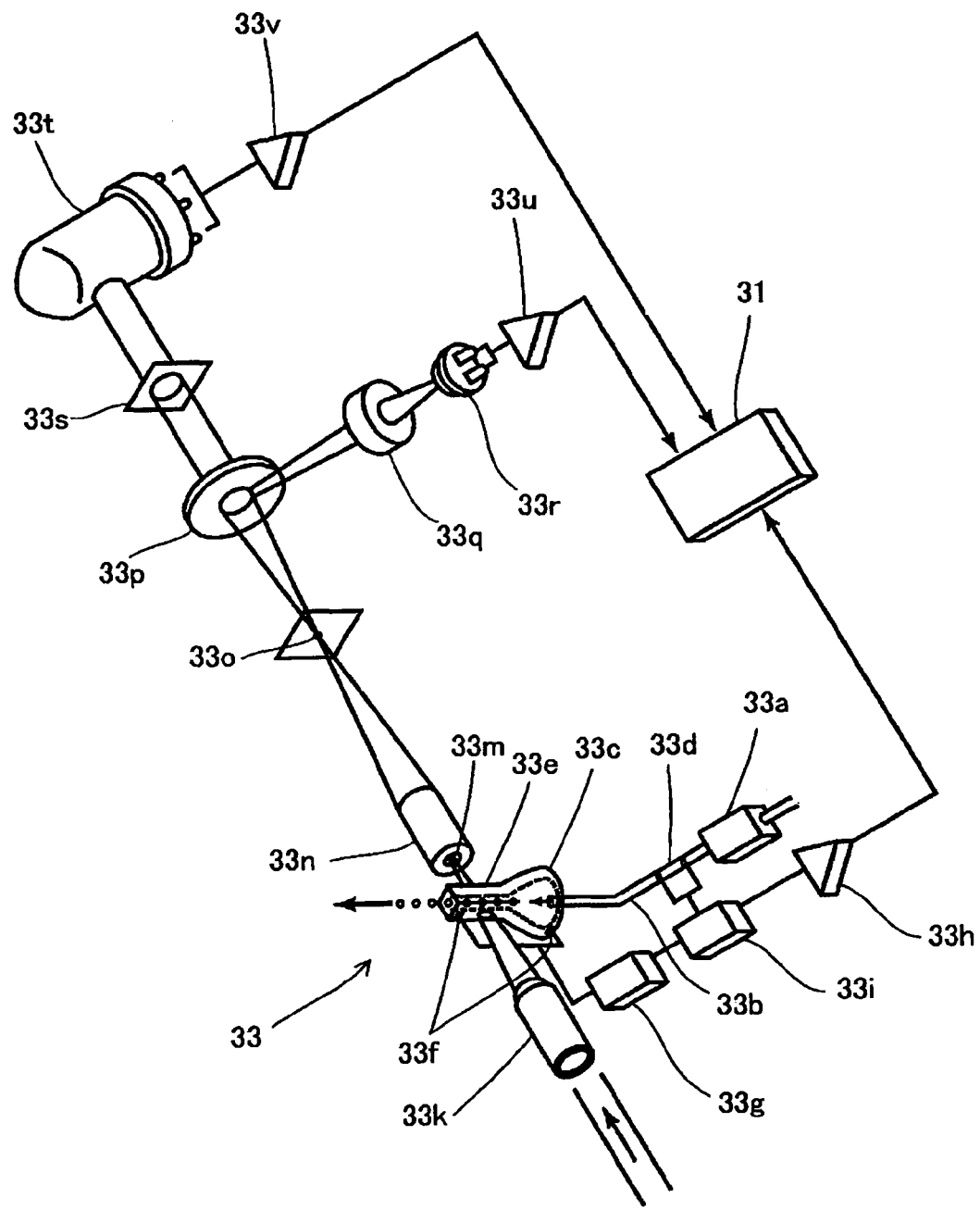
FIG. 5 is a schematic view showing the structure of the main part of the analyzer for analyzing urinary particles.

FIG. 5 is a schematic view showing the structure of the main part of the analyzer for analyzing urinary particles. The measuring unit 33 has a reaction unit 33a; a urine specimen (sample) transported by the conveyance device 5 is suctioned by a sample suction pipette (not shown in the drawing), and the suctioned sample is introduced into the reaction unit 33a together with dilution solution and stain solution. In the reaction unit 33a, the sample is mixed with the dilution solution and stain solution, such that the urine is diluted four fold. The reaction unit 33a has a temperature controller provided with a heater such as a thermistor or the like, so as to control the temperature at a constant 35° C. while mixing the sample to accomplish staining for ten seconds.

A flow path 33b extends from the reaction unit 33a, and a sheath flow cell 33c is provided at the end of the flow path 33b. A conductivity sensor 33d is also provided within the flow path 33b. The sample that has been diluted and stained in the reaction unit 33a flows through the flow path 33b to the sheath flow cell 33c. A sheath fluid chamber not shown in the drawing is provided in the measuring unit 33, such that sheath fluid stored in the sheath fluid chamber can be supplied to the sheath flow cell 33c. The sample flows in the sheath flow cell 33c surrounded by the sheath fluid. An orifice 33e is provided in the sheath flow cell 33c, such that the sample flow is constricted by the orifice 33e and the particles (tangible materials) contained in the sample pass through the orifice 33e one at a time. A pair of electrodes 33f are disposed in the sheath flow cell 33c so as to have the orifice 33e situated therebetween. These electrodes 33f are connected to a direct current (DC) power supply 33g, so as to supply a DC current between the electrodes 33f. Then, the impedance between the electrodes 33f is detected while the DC current flows from the DC power supply 33g. Electrical resistance signals representing the change in impedance are amplified by an amplifier 33h and transmitted to the controller 31. The electrical resistance signal reflects the particle volume information, such that the volume of the particle can be obtained when the electrical resistance signal is subjected to signal processing by the controller 31.

Figure 6:
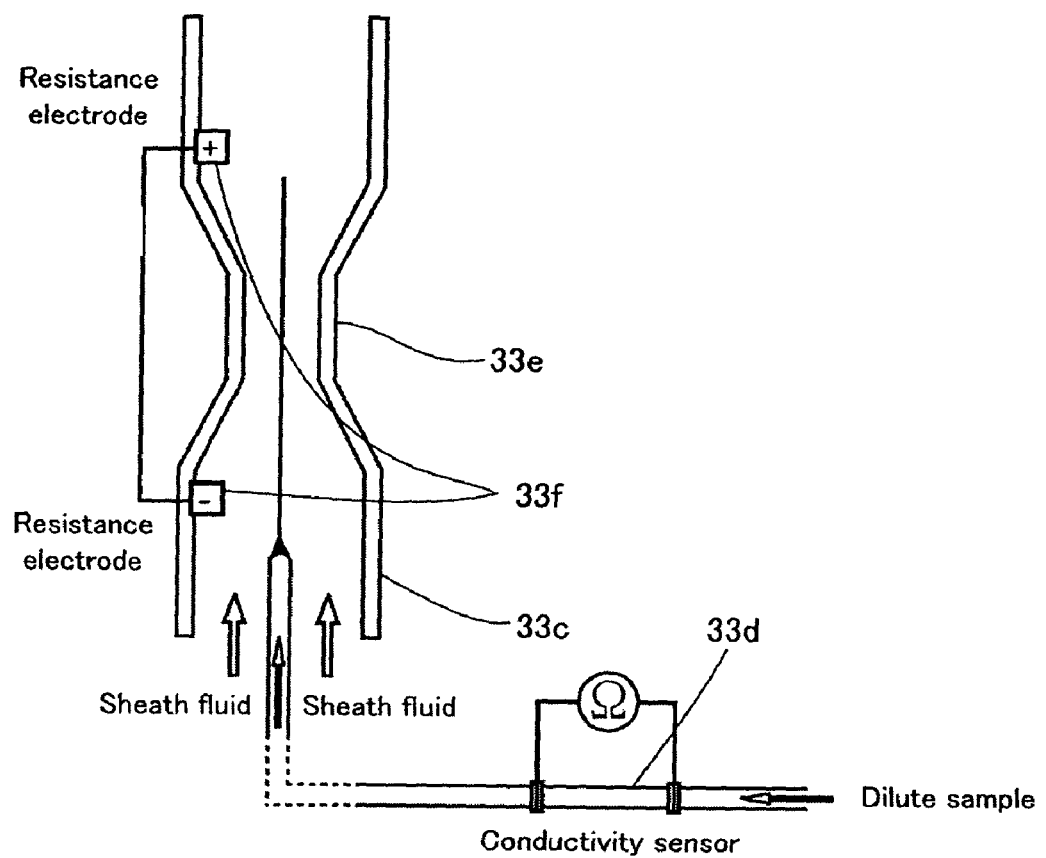
FIG. 6 is a schematic view showing the structure of the sheath flow cell and vicinity describing the impedance measurement sensitivity adjustment for conductivity measurement.
Figure 7:
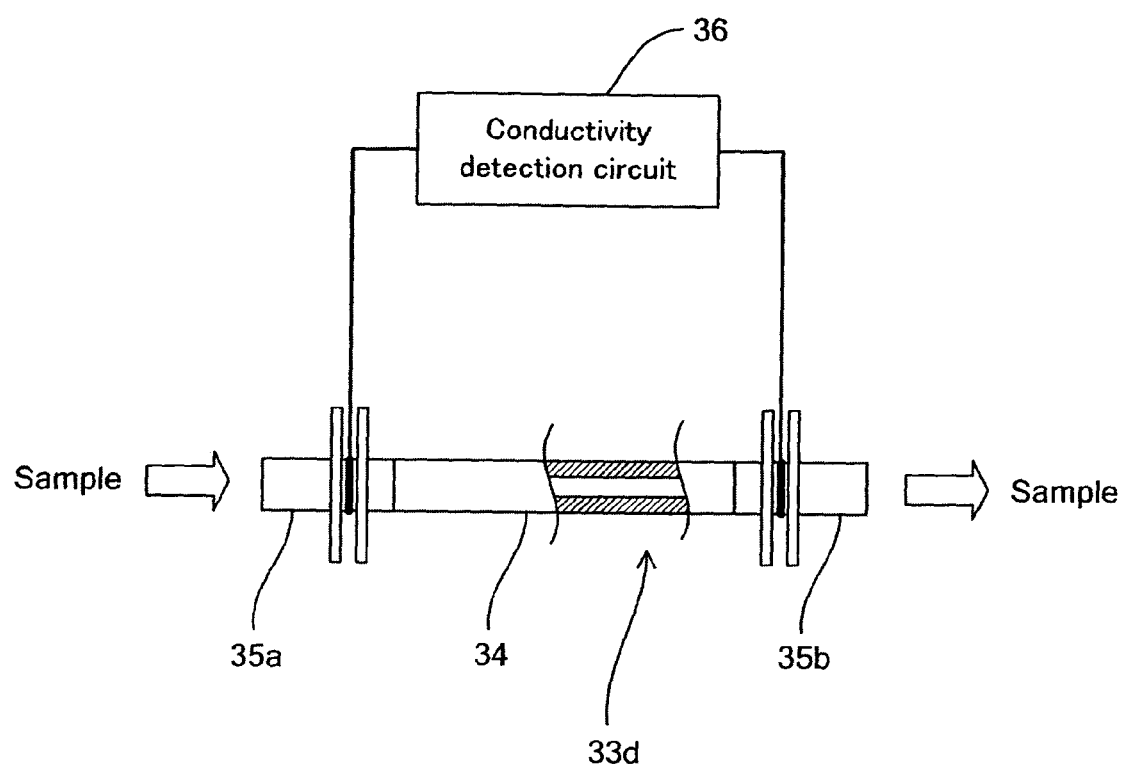
FIG. 7 is a partial section side view showing the structure of a conductivity sensor of an embodiment of the present invention.

Furthermore, the sample passes through the flow path 33b before being supplied to the sheath flow cell 33c, and the conductivity is detected by the conductivity sensor 33d. The conductivity detected by the conductivity sensor 33d is transmitted to a current control circuit 33i, and the current control circuit 33i controls the output current of the DC power supply 33g based on this detected conductivity. FIG. 6 is a schematic view showing the structure of the sheath flow cell and vicinity describing the impedance measurement sensitivity adjustment for conductivity measurement; and FIG. 7 is a partial section side view showing the structure of the conductivity sensor 33d. The conductivity of urine samples differs for each sample, and when the conductivity of the sample changes, the current changes between the electrodes 33f regardless of the presence or absence of the passing particles. Therefore, impedance detection sensitivity is affected and accurate particle volume information cannot be obtained. Thus, in the measuring unit 33, the electrical conductance of the sample is maintained within a constant range by dilution using a urinopack (dilution solution), and the conductivity is measured before the dilute sample enters the sheath flow cell 33c, and the sensitivity is regularly adjusted to correct the detection current in accordance with this conductivity value. The structure of the conductivity sensor 33d is described below with reference to FIG. 7. The conductivity sensor 33d has an approximately cylindrical shape overall, and is mainly configured by a insulating tube 34 formed of an insulating body such as synthetic resin, ceramic or the like, and metal electrodes 35a and 35b mounted on bilateral ends of the insulating tube 34. The metal electrodes 35a and 35b are annular in shape and have the same internal diameter as the insulating tube 34, and are mounted coaxially on the insulating tube 34. In this way a hollow space of the same internal diameter is formed the entire length in the conductivity sensor 33d. A conductivity detection circuit 36 is connected to the metal electrodes 35a and 35b, such that when sample flows through the hollow interior, a sine wave current of approximately 1 kHz is applied between the metal electrodes 35a and 35b, and the conductivity detection circuit 36 rectified and integrates the current flowing to the sample flowing in the hollow interior, and detects a voltage proportional to the conductivity of the sample. Then, the obtained conductivity signal is transmitted to the current control circuit 33i.

Furthermore, the current control circuit 33i outputs the input conductivity signal to the controller 31. When the temperature changes, the conductivity changes in connection with the temperature fluctuation because substances ionize differently.

An argon laser light source is arranged in the measuring unit 33 so as to emit laser light toward the orifice 33e of the sheath flow cell 33c. An illumination lens 33k configured by a plurality of lenses is arranged between the argon laser light source and the sheath flow cell 33c. Parallel beams emitted from the argon laser light source are condensed on a beam spot by the illumination lens 33k. The beam spot is elliptical in shape, and the focal point is in the center of the sheath flow cell 33c. A collector lens 33n, which is provided with a beam stopper 33m, is arranged on the optical axis of the laser light emitted from the argon laser light source so as to be opposite the illumination lens 33k with the sheath flow cell 33c disposed therebetween, such that the direct light from the argon laser light source is blocked by the beam stopper 33m.

When the sample flows through the sheath flow cell 33c, optical signals of the scattered light and fluorescent light are generated by the laser light. The forward signal light is collected by the collector lens 33n and transmitted to the latter stage light-receiving system. A pinhole 33o is provided in the light-receiving system, and a dichroic filter (shown as a dichroic mirror 33p) is provided on the downstream side of the optical axis. After the stray light (light outside the measurement range) is removed by the pinhole 33o, the signal light transmitted from the collector lens 33n separated into a scattered light component and fluorescent light component by the dichroic mirror 33p. A scattered light converging lens 33q and photodiode 33r are provided in a lateral direction (direction intersecting the optical axis direction) of the dichroic mirror 33p, and a color glass filter 33s and a photomultiplier 33t are provided on the downstream side of the optical axis of the dichroic mirror 33p. The scattered light component separated by the dichroic mirror 33p is converged by the lens 33q, and subsequently subjected to photoelectric conversion by the photodiode 33r, which generates an electric signal (scattered light signal) that is amplified by an amplifier 33u and output to the controller 31. The scattered light signal reflects information pertaining to the size of the particle, and the cross section volume and length of the particle are obtained when the controller 31 subjects the scattered light signal to signal processing. The fluorescent light produced by the dichroic mirror 33p undergoes wavelength selection by the color glass filter 33s, and is subsequently subjected to photoelectric conversion by the photomultiplier 33t, which generates an electric signal (fluorescent light signal) that is amplified by an amplifier 33v and output to the controller 31. The fluorescent light color element used has the characteristics of specifically staining the nucleus of the particle, such that the staining characteristics and length of the stained part of the particle is obtained when the controller 31 subjects the fluorescent light signal to signal processing.

In this way electrical resistance signals, conductivity signals, scattered light signals, and fluorescent light signals are transmitted from the measuring unit 33 to the controller 31. The controller 31 processes the electrical resistance signals, scattered light signals, and fluorescent light signals to obtain the red blood cell concentration, white blood cell concentration, bacteria concentration, cast concentration, and epithelial cell concentration in the sample, and the measurement result data are transmitted from the communication unit 32 to the computer 6. The urinary particle analyzer 3 is configured such that the conductivity measurement result data obtained by the controller 31 are also transmitted from the communication unit 32 to the computer 6.

The structures of the conveyance devices 4 and 5 are described below. As shown in FIG. 2, the conveyance device 4 is provided with a conveyor 41 for transporting a sample rack 7a that accommodates a plurality (for example, ten) sample containers 7 containing samples, an input panel 42 for allowing a user to input various setting values and the like for the conveyance device 4, and an LCD panel 43 for displaying the setting conditions and the like for the conveyance device 4. The conveyor 41 is configured by a sending unit 44 in which a user places a sample rack 7a containing samples for analysis, horizontal conveyor 45 that moves the sample containers 7 accommodated in the sample rack 7a placed in the sending unit 44 to the measurement position for measurement by the first measuring unit 23 and second measuring unit 24 of the urine qualitative analyzer 2, and discharge unit 46 for moving the sample rack 7a to the conveyance device 5 after measurements have been performed by the urine qualitative analyzer 2. The conveyance device 5 is provided with a sending unit 51 for transporting a sample rack 7a accommodating a plurality of sample containers 7 containing samples, input panel 52 to allow a user to input various setting values and the like for the conveyance device 5, and an LCD panel 53 for displaying the setting conditions of the conveyance device 5. The conveyor 51 is configured by a sending unit 54 for receiving a sample rack 7a from the conveyance device 4, horizontal conveyor 55 for moving the sample containers 7 accommodated in the received sample rack 7a to the measurement position for measurement by the measuring unit 33 of the urinary particle analyzer 3, and collection unit 56 for collecting the sample rack 7a after measurements have been performed by the urinary particle analyzer 3.

Figure 8:
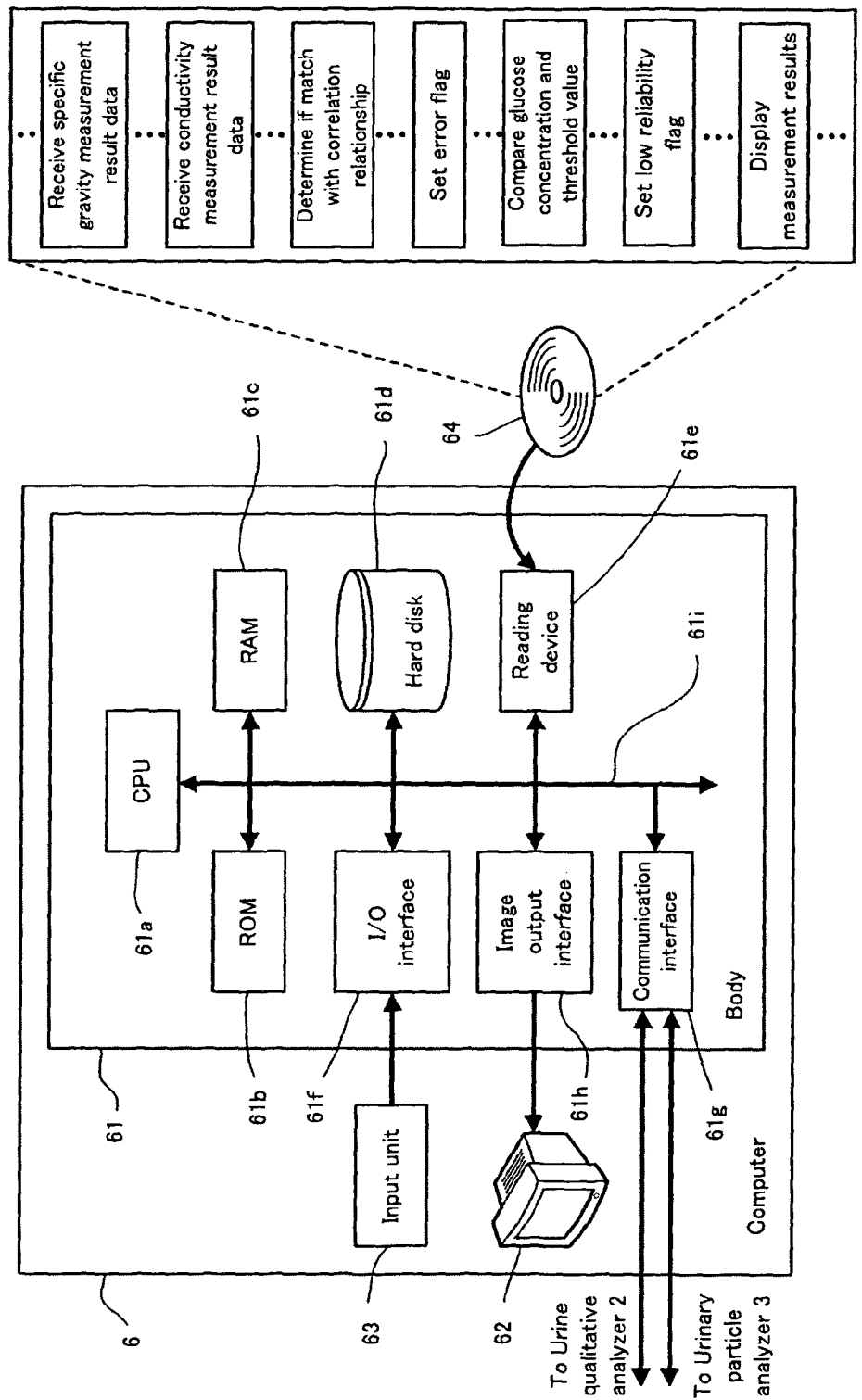
FIG. 8 is a block diagram showing the structure of a computer in the system for checking measurement results of an embodiment of the present invention.

The structure of the computer 6 is described below. FIG. 8 is a block diagram showing the structure of a computer in the system for checking measurement results of an embodiment of the present invention. The computer 6 is mainly configured by a body 61, image display unit 62, and input unit 63. The body 61 is mainly configured by a CPU 61a, ROM 61b, RAM 61c, hard disk 61d, reading device 61e, input/output (I/O) interface 61f, communication interface 61g, and image output interface 61h; the CPU 61a, ROM 61b, RAM 61c, hard disk 61d, reading device 61e, I/O interface 61f, communication interface 61g, and image output interface 61h are connected by a bus 61i.

The CPU 61a is capable of executing computer programs stored in the ROM 61b and computer programs loaded in the RAM 61c. The computer 6 functions as the apparatus for checking measurement results of the present invention by the CPU 61a executing these computer programs in a manner described later.

The ROM 61b may be a mask ROM, PROM, EPROM, EEPROM or the like, that stores computer programs executed by the CPU 61a and the data used by these computer programs.

The RAM 61c is an SRAM, DRAM or the like. The RAM 61c is used when reading the computer programs stored in the ROM 61b and on the hard disk 61d. The RAM 61c is used as the work area of the CPU 61a when these computer programs are executed.

The hard disk 61d contains an installed operating system and applications and the like, including various computer programs executed by the CPU 61a and data used in the execution of these computer programs.

The reading device 61e is a floppy disk drive, CD-ROM drive, DVD-ROM drive or the like, and is capable of reading computer programs and data recorded on a transportable recording medium 64. The transportable recording medium 64 stores a computer program that provides the functions of the apparatus for checking measurement results of the present invention; the computer 6 reads this computer program of the present invention from the transportable recording medium 64, and installs this computer program on the hard disk 61d.

This computer program may also be provided over an electrical communication line from an external apparatus capable of communicating with the computer 6 over an electrical communication line (either wire line, or wireless) without being provided by the transportable recording medium 64. For example, this computer program may be stored on the hard disk of a server computer connected to the internet, such that the computer 6 can access the server computer and download the computer program and install the computer program on the hard disk 61d.

The operating system installed on the hard disk 61d to provide a graphical user interface environment may be, for example, the Windows (registered trademark) operating system produced by the Microsoft Corporation of the USA. In the following description, the computer program of the present embodiment operates under the aforesaid operating system.

The hard disk 61d also stores a crosscheck table representing correlative relationships between occult blood concentration and red blood cell concentration, correlative relationship of white blood cell concentration, correlative relationships between protein concentration and cast concentration, correlative relationships between nitrite concentration and bacteria concentration, and correlative relationships between conductivity and specific gravity.

In urine qualitative analysis, for example, the occult blood concentration will react to the negative side due to ascorbic acid content and the like, and react to the positive side due to hypochlorous acid content and the like. It is known that there is a high degree of correlation between occult blood concentration and red blood cell concentration, between white blood cell concentration and white blood cell concentration, between protein concentration and cast concentration, between nitrite concentration and bacteria concentration, and between specific gravity and conductivity. Accordingly, the measurement results of the urine qualitative analyzer 3 and the urinary particle analyzer 4 can checked using these correlative relationships so as to discriminate measurement results that have low reliability.

Figure 9:
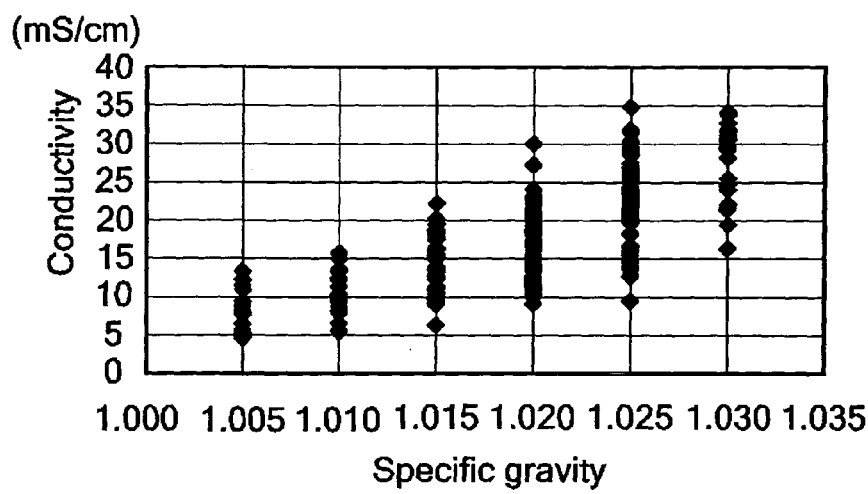
FIG. 9 is a graph showing the correlative relationships of urine specific gravity and urine conductivity.

The correlative relationships between specific gravity and conductivity are described below. FIG. 9 is a graph showing the correlative relationships of specific gravity and conductivity. In FIG. 9, the vertical axis represents conductivity (mS/cm), and the horizontal axis represents specific gravity. FIG. 9 shows the relationship between conductivity relative to specific gravity measured result using a test paper. In measurements of specific gravity by test paper, specific gravity is expressed colorimetrically in seven levels at 0.005 intervals between 1.000 to 1.030. The measurement results for specific gravity and conductivity for a plurality of samples are plotted in FIG. 9. As shown in FIG. 9, when the specific gravity is 1.005, the conductivity falls within a range of 5~12 mS/cm; and when the specific gravity is 1.010, the conductivity falls within a range of 5~16.6 mS/cm. Similarly, when the specific gravity is 1.015, 1.020, 1.025, and 1.030, the conductivity falls within the range of 7.5~21 mS/cm, 12~26 mS/cm, 16.5~30 mS/cm, and 21~35 mS/cm, respectively.

Figure 10:
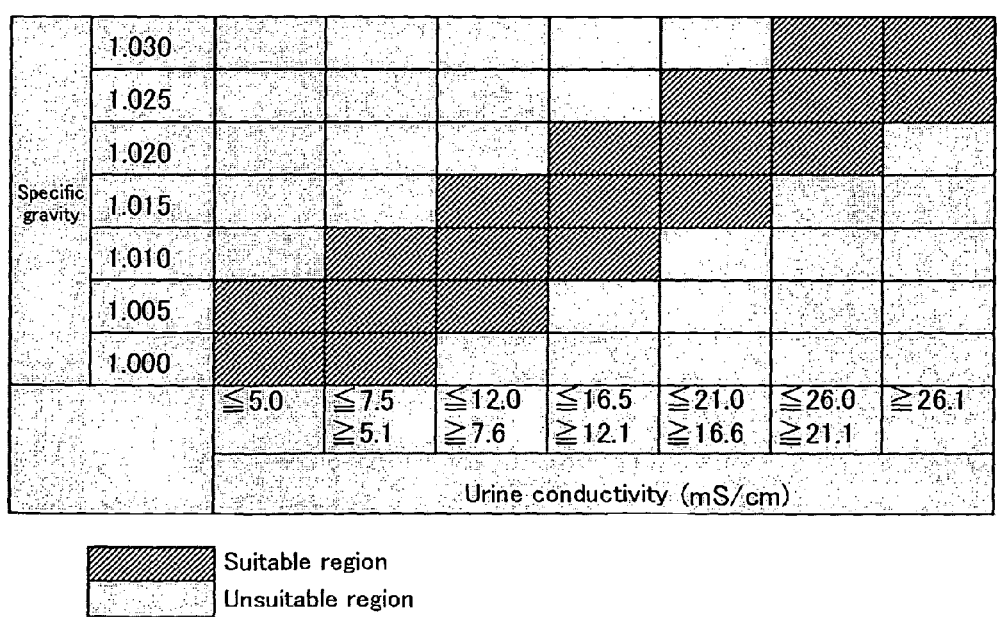
FIG. 10 is a graph showing a crosscheck table for specific gravity and conductivity of the present embodiment.

In the present embodiment, a crosscheck table for specific gravity and conductivity described below is set as a default. FIG. 10 is a graph showing a crosscheck table for specific gravity and conductivity of the present embodiment. In FIG. 10, the vertical axis represents specific gravity, and the horizontal axis represents conductivity (mS/cm). This crosscheck table divides measurement values of corresponding measurement items into suitable intervals (ranks), and each measurement item is allocated a suitable region and unsuitable region. Corresponding measurement results among the measurement results of the urine qualitative analyzer 2 and the measurement results of the urinary particle analyzer 3 are determined to conform to the correlative relationship of both measurement results when they are in the suitable region, and are determined to not conform to the correlative relationship when in the unsuitable region. FIG. 10 shows the specific gravity and conductivity of corresponding measurement items; specific gravity is divided into ranks at 0.005 intervals between 1.000 to 1.030, and the range of conductivity above 0 is respectively divided into ranks 0~5.0 mS/cm, 5.1~7.5 mS/cm, 7.6~12.0 mS/cm, 12.1~16.5 mS/cm, 16.6~21.0 mS/cm, and 21.1~26.0 mS/cm. When the specific gravity is in the rank 1.0000~1.005, the suitable region of conductivity is the rank 0~5.0 mS/cm; when specific gravity is in the rank 1.006~1.010, the suitable region of conductivity is the rank 0~12.0 mS/cm; when specific gravity is in the rank 1.011~1.015, the suitable region of conductivity is the rank 5.1~16.5 mS/cm; when specific gravity is in the rank 1.016~1.020, the suitable region of conductivity is the rank 7.6~21.0 mS/cm; when specific gravity is in the rank 1.021~1.025, the suitable region of conductivity is the rank 12.1~26.0 mS/cm; when specific gravity is in the rank 1.026~1.030, the suitable region of conductivity is the rank 16.6 and above; when specific gravity is in the rank of 1.031 and above, the suitable range of conductivity is the rank 21.1 and above. Regarding other measurement items in the crosscheck table, the measurement items of the urine qualitative analyzer 2 are classified beforehand into ranks corresponding to (−), (±), (+), (2+), (3+), . . . (7+), and measurement items of the urinary particle analyzer 3 are classified beforehand in suitable ranks.

Figure 11:
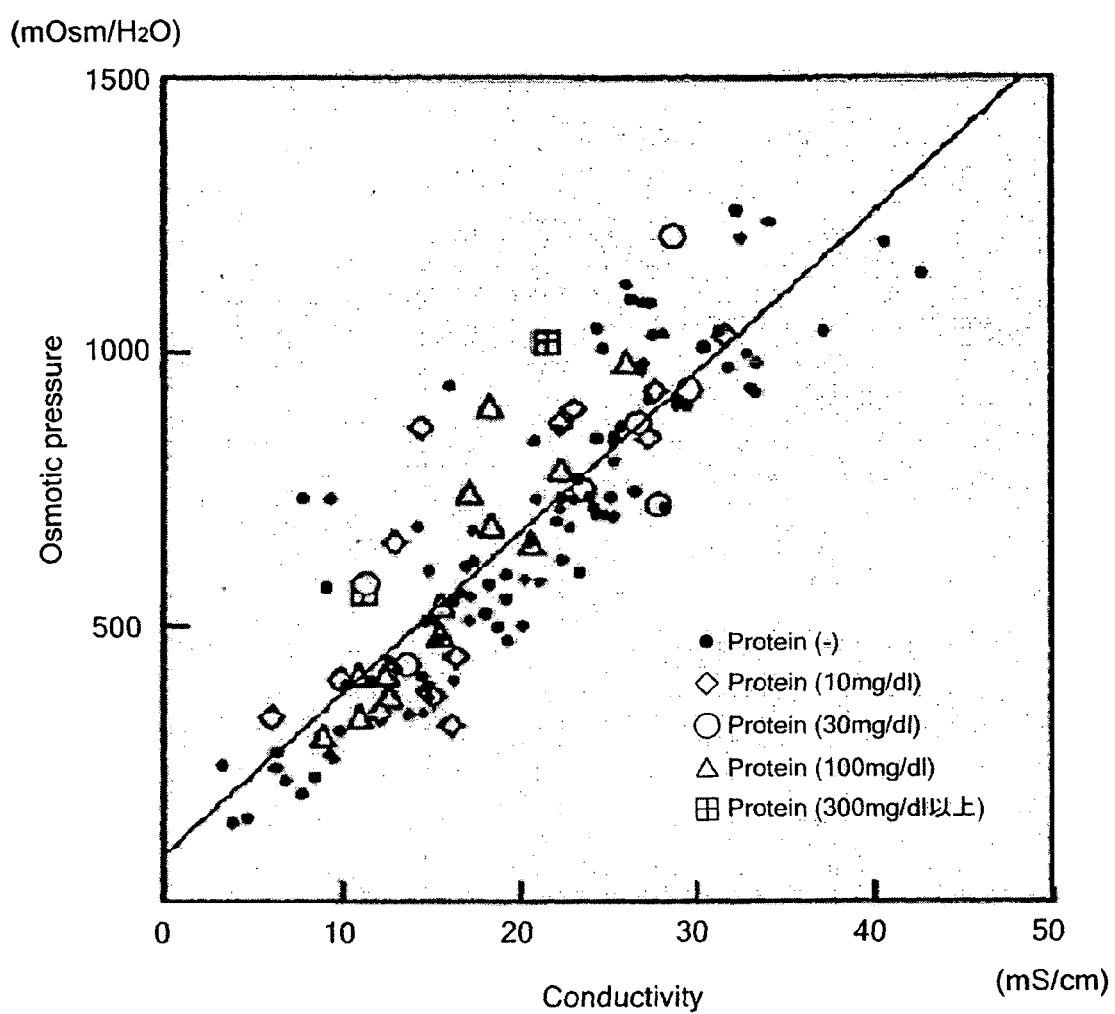
FIG. 11 is a graph showing experimental results of investigations of the influence of conductivity on urine protein concentration.
Figure 12:
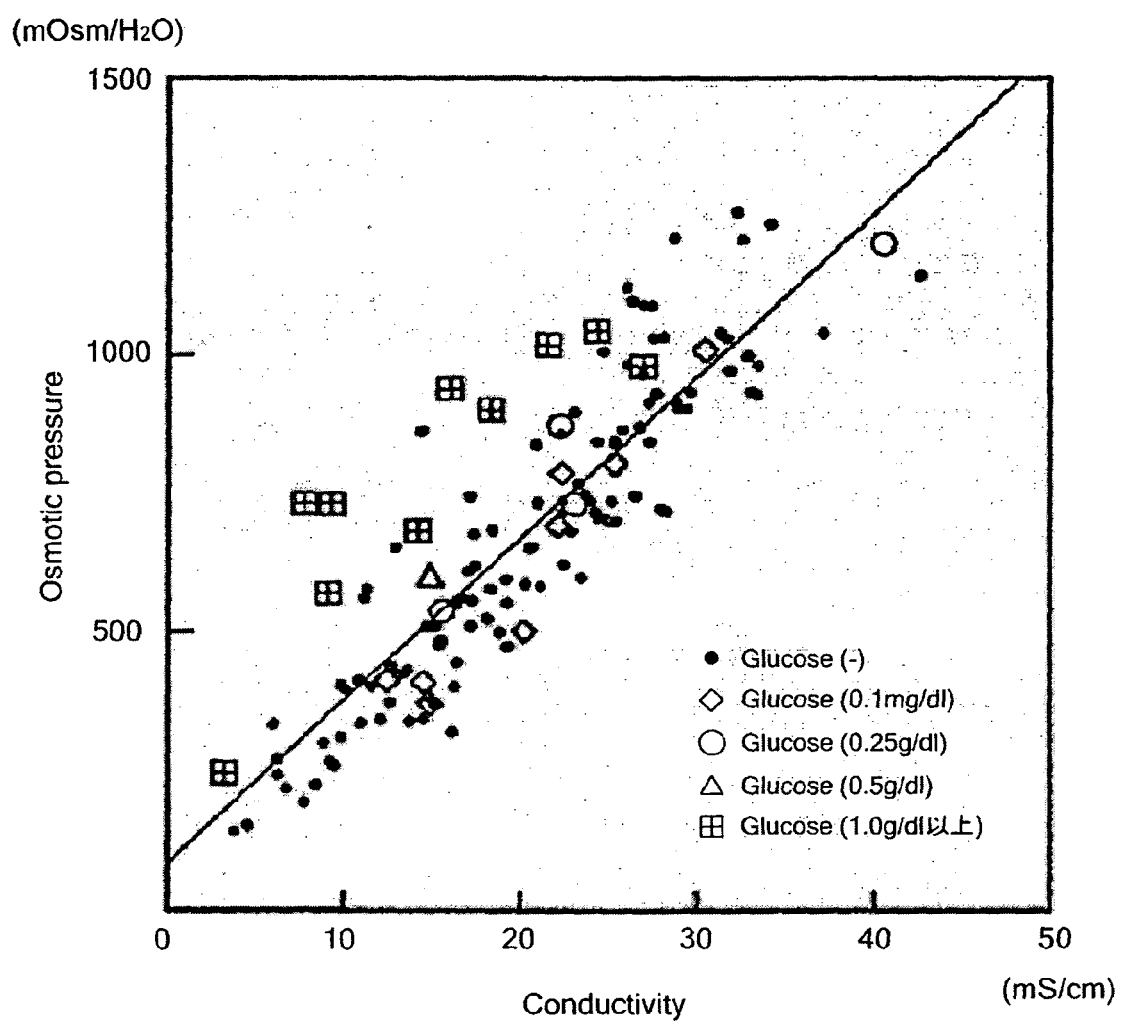
FIG. 12 is a graph showing experimental results of investigations of the influence of conductivity on urine glucose concentration.

The hard disk 61d stores threshold values related to glucose concentration measurement results that are used to determine whether or not the conductivity measured by the urinary particle analyzer 3 has low reliability. The present inventors have conducted experimental investigations on the influence of urine sugar concentration and protein concentration on conductivity. FIG. 11 is a graph showing the results of experiments concerning protein concentration, and FIG. 12 is a graph showing results of experiments concerning glucose concentration. In FIGS. 11 and 12, the vertical axis represents the osmotic pressure (mOsm/H20), and the horizontal axis represents conductivity (mS/cm). Specific gravity and osmotic pressure are known to be highly correlated, and to have approximately equivalent clinical significance. Accordingly, the relationship between conductivity and osmotic pressure was investigated rather than investigate the relationship between conductivity and specific gravity. In FIG. 11, the measurement results of conductivity and osmotic pressure when protein was not detected in the sample are represented by a dot; the measurement results when protein was detected in the sample at approximately 15 mg/dl are represented by a diamond; measurement results when protein was detected in the sample at approximately 30 mg/dl are represented by a circle; measurement results when protein was detected in the sample at approximately 100 mg/dl are represented by a triangle; and measurement results when protein was detected in a sample at approximately 300 mg/di or higher are represented by squares. As shown in FIG. 11, samples in which protein was detected at 300 mg/dl or higher are largely divergent from the measurement result line representing a correlative relationship between osmotic pressure and conductivity, and it is understood that such measurement results have low reliability. In these experimental results, samples in which detected protein was approximately 15 mg/dl samples in which detected protein was approximately 30 mg/dl, samples in which detected protein was approximately 100 mg/dl also largely diverged from the line representing a correlative relationship.

In FIG. 12, the measurement results of conductivity and osmotic pressure when glucose was not detected in the sample are represented by a dot; the measurement results when glucose was detected in the sample at approximately 0.1 g/dl are represented by a diamond; measurement results when glucose was detected in the sample at approximately 0.25 g/dl are represented by a circle; measurement results when glucose was detected in the sample at approximately 0.5 g/dl are represented by a triangle; and measurement results when glucose was detected in a sample at approximately 1.0 g/dl or higher are represented by squares. As shown in FIG. 12, samples in which glucose was detected at 1.0 g/dl or higher are largely divergent from the line representing a correlative relationship between osmotic pressure and conductivity, and it is understood that these measurement results have low reliability. In comparing these experimental results with the protein experimental results, is can be understood that the measurement results for samples that have a high glucose concentration diverge even more markedly from the line representing a correlation. Furthermore, it can be understood that the measurement results for samples other than those samples in which the detected glucose concentration was 1.0 g/dl or higher did not diverge greatly from the line representing a correlation.

Figure 13:
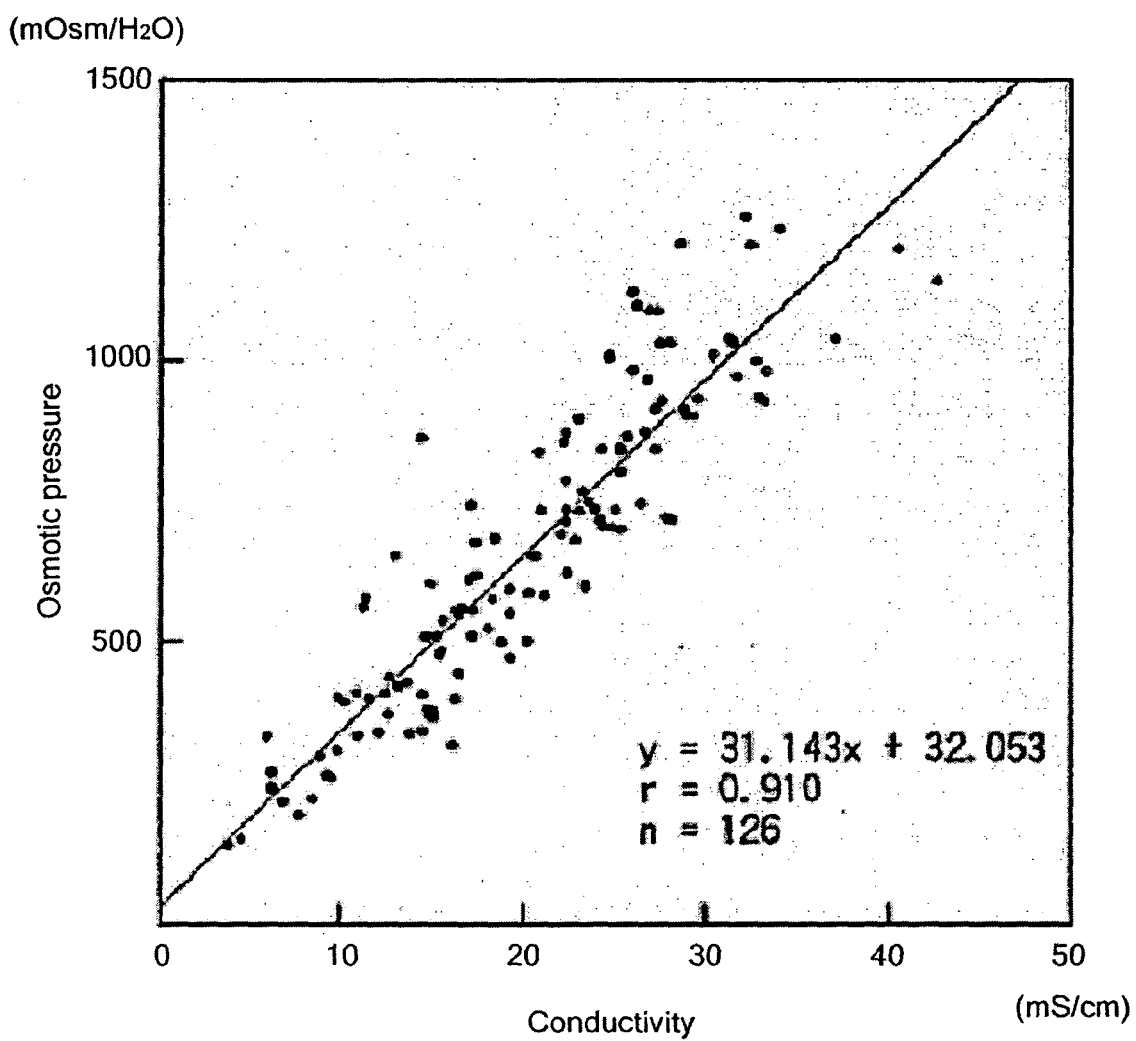
FIG. 13 is a graph in which the measurement results of samples with high glucose concentration are excluded from the correlation graph of conductivity and osmotic shown in FIG. 12.

FIG. 13 is a graph in which the measurement results of samples with high glucose concentration are excluded from the correlation graph of conductivity and osmotic shown in FIG. 12. It can be understood from FIG. 13 that the correlation is clearly greater compared to the correlative relationships shown in FIGS. 11 and 12. The correlation coefficient is 0.91 in the experimental results of FIG. 13, and it is understood that these results are an improvement compared to the correlation coefficient of 0.869 in the experimental results of FIGS. 11 and 12. These results are thought to have been caused by reduced conductivity in a nonconductor as these concentrations increased since protein and sugar are not electrolytes.

In this way the present inventors observed the measurement results for conductivity in samples that had a high protein or high sugar (including glucose) concentration diverged from a correlation with osmotic pressure (specific gravity) in urine with indication of serious renal dysfunction, and that such measurement results had low reliability as clinical data. In the present embodiment, a threshold value for glucose concentration measurement result set at 1.0 g/dl is used to determine whether or not the conductivity measured by the urinary particle analyzer 3 is low reliability.

The I/O interface 61f is configured by, for example, a serial interface such as a USB, IEEE1394, RS-232C or the like, parallel interface such as a SCSI, IDE, IEEE1284 or the like, and analog interface such as a D/A converter, A/D converter or the like. An input unit 63 such as a keyboard and mouse is connected to the I/O interface 61f such that a user can use the input unit 63 to input data to the computer 6.

The communication interface 61g is, for example, an Ethernet (trademark) interface, such that the computer 6 can transmit and receive data with the urine qualitative analyzer 2, urinary particle analyzer 3, and conveyance devices 4 and 5 using the communication interface 61g and a predetermined communication protocol.

The image output interface 61h is connected to the image display unit 62 such as an LCD or CRT or the like, and outputs image signals corresponding to the image data transmitted from the CPU 61a to the image display unit 62. The image display unit 62 displays images (screens) in accordance with the input image signals.

The operation of the system 1 for checking measurement results of the present embodiment is described below. First, the sample rack 7a accommodating a plurality of sample containers 7 containing samples (urine) is automatically conveyed to the measuring position at the front side of the urine qualitative analyzer 2. Specifically, the sample rack 7a accommodating a plurality of sample containers 7 containing samples is placed on the sending unit 44 of the conveyance device 4. Then, the start key provided on the input panel 42 is pressed. In this way the operation of the conveyance device 4 begins, and the sample rack 7a placed in the sending unit 44 of the conveyance device 4 is transported to the horizontal conveyor 45. Next, the sample containers 7 accommodated in the sample rack 7a are transported to the measuring position of the urine qualitative analyzer 2 when the horizontal conveyor 45 sequentially performs horizontal conveyance of the sample rack 7a at a pitch corresponding to one sample container 7. In the first measuring unit 23 and second measuring unit 24 of the urine qualitative analyzer 2, the samples contained in the sample containers accommodated in the sample rack 7a are sequentially measured. Thereafter, the sample rack 7a is transported from the horizontal conveyor 45 to the discharge unit 46, and transported to the sending unit 54 of the conveyance device 5. Then, the conveyance device 5 starts operation when it detects the transport of the sample rack 7a to the sending unit 54 by means of a sensor provided on the sending unit 54.

The sample rack 7a transported by the sending unit 54 of the conveyance device 5 is conveyed to the horizontal conveyor 55 of the conveyance device 5. Next, the sample containers 7 accommodated in the sample rack 7a are transported to the measuring position of the urinary particle analyzer 3 when the horizontal conveyor 55 sequentially performs horizontal conveyance of the sample rack 7a at a pitch corresponding to one sample container 7. In the measuring unit 33 of the urinary particle analyzer 3, the samples contained in the sample containers 7 accommodated in the sample rack 7a are sequentially measured. Thereafter, the sample rack 7a is transported from the horizontal conveyor 55 to the collection unit 56. This operation is sequentially performed for each sample rack 7a.

Figure 14:
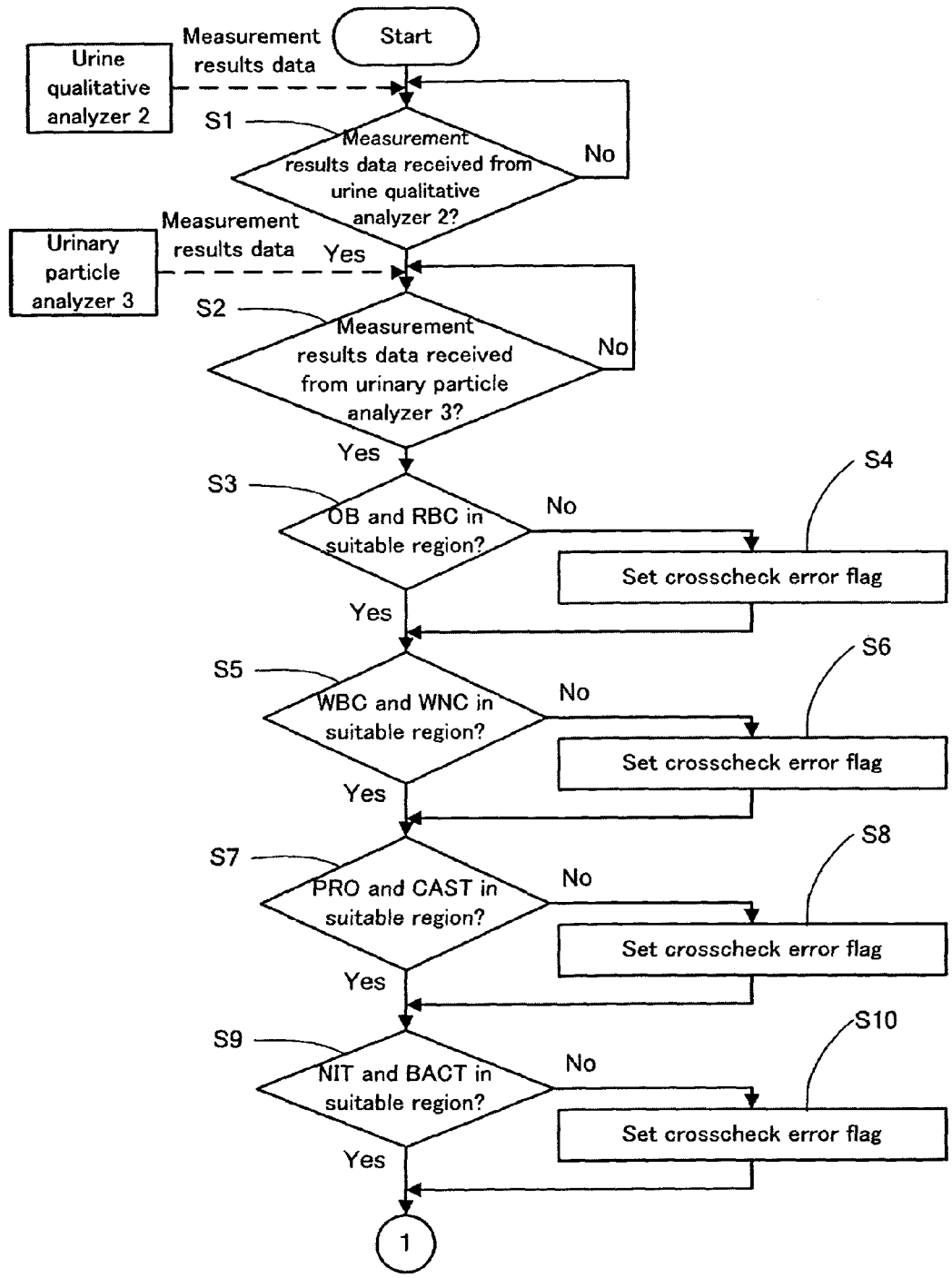
FIG. 14 is a flow chart showing the sequence of the crosscheck process by the computer program of an embodiment of the present invention.
Figure 15:
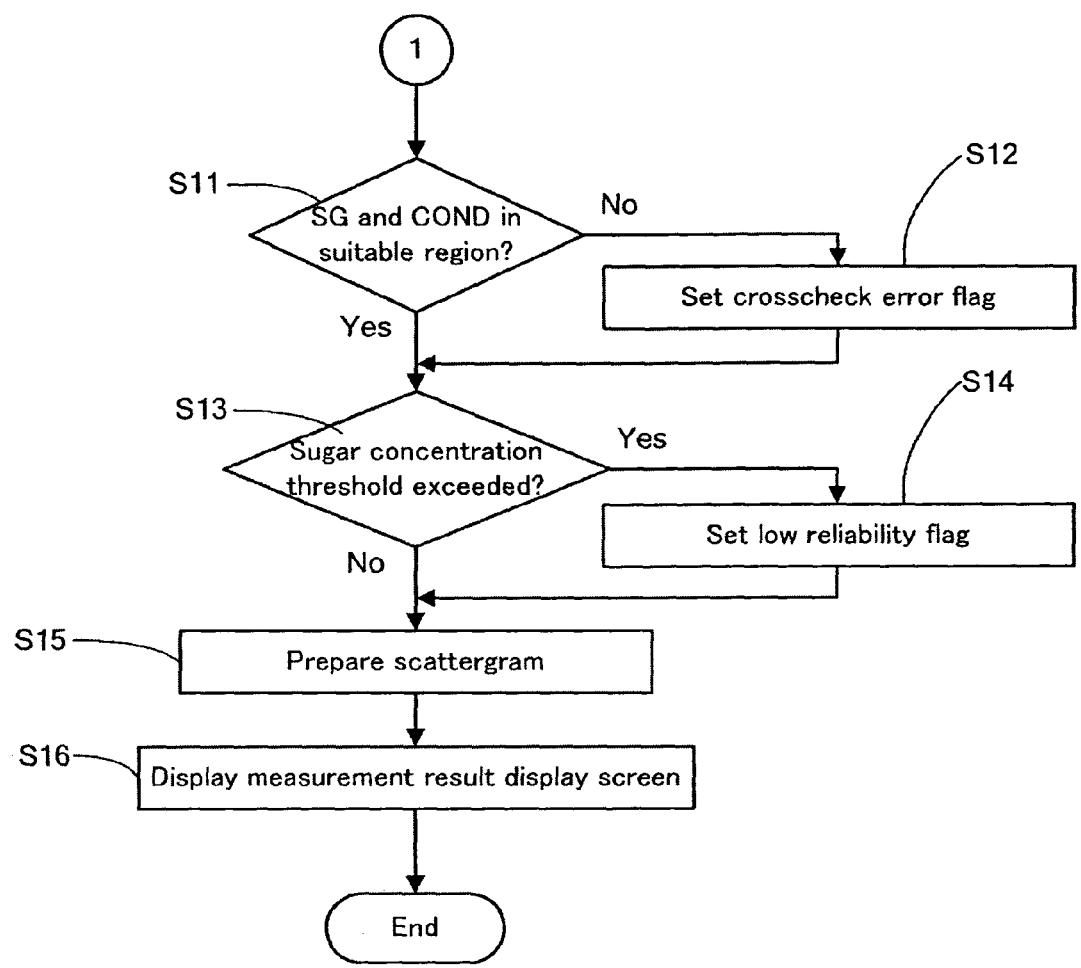
FIG. 15 is a flow chart showing the sequence of the crosscheck process by the computer program of an embodiment of the present invention.

In this way the urine qualitative analyzer 2 and the urinary particle analyzer 3 measure the same sample, and the obtained measurement result data are transmitted to the computer 6. Then, the computer 6 executes the crosscheck process. The crosscheck process executed by the computer 6 is described below. FIGS. 14 and 15 are flow charts showing the sequence of the crosscheck process accomplished by the computer program of the embodiment of the present invention executed by the computer 6.a crosscheck error flag corresponding to each measurement item described below, and a low reliability flag are set to default values when cleared. First, the CPU 61a of the computer 6 awaits reception of measurement result data from the urine qualitative analyzer 2 (step S1). When measurement result data have been received (step S1: YES), the CPU 61a awaits reception of measurement result data from the urinary particle analyzer 3 (step S2). When the measurement result data has been received in step S2 (step S2: YES), the CPU 61a determines whether or not the occult blood concentration measurement result (OB) and red blood cell concentration measurement result (RBC) are in the suitable regions in the crosscheck table that represents the correlative relationships of these measurement items (step S3). When the occult blood concentration measurement result (OB) and the red blood cell concentration measurement result (RBC) are in unsuitable regions of the crosscheck table (step S3: NO), the CPU 61a sets the crosscheck error table relating to the occult blood concentration measurement result (step S4).

Next, the CPU 61a determines whether or not the white blood cell concentration measurement result (WBC) of the urine qualitative analyzer 2 and the white blood cell concentration measurement results (WBC) of the urinary particle analyzer 3 are in the suitable regions in the crosscheck table representing the correlative relationship of these measurement items (step S5). When both measurement results are in unsuitable regions of the crosscheck table (step S5: NO), the CPU 61a sets the crosscheck error table relating to the white blood cell concentration of the urine qualitative analyzer 2 (step S6).

The CPU 61a then determines whether or not the protein concentration measurement result (PRO) and the cast concentration measurement result (CAST) are in the suitable regions in the crosscheck table representing the correlative relationship of these measurement items (step S7). When both measurement results are in unsuitable regions of the crosscheck table (step S7: NO), the CPU 61a sets the crosscheck error table relating to the white protein concentration measurement result (step S8).

Then, the CPU 61a determines whether or not the nitrite concentration measurement result (NIT) and the bacteria concentration measurement result (BACT) are in the suitable regions in the crosscheck table representing the correlative relationship of these measurement items (step S9). When both measurement results are in unsuitable regions of the crosscheck table (step S9: NO), the CPU 61a sets the crosscheck error table relating to the nitrite concentration measurement result (step S10).

The CPU 61a then determines whether or not the specific gravity measurement result (SG) and conductivity measurement result (COND) are in the suitable regions of the crosscheck table representing the correlative relationship of the measurement items (step S11). When both measurement results are in unsuitable regions of the crosscheck table (step S11: NO), the CPU 61a sets the crosscheck error table relating to the specific gravity measurement result (step S12).

The CPU 61a then compares the glucose concentration measurement result with a threshold value used to determine whether or not the conductivity measured by the urinary particle analyzer 3 has low reliability (step S13). When the glucose concentration measurement result exceeds the threshold in step S13 (step S13: NO), the CPU 61a sets the low reliability flag relative to the conductivity measurement value (step S14).

The CPU 61a then prepares a scattergram using the measurement results of the urinary particle analyzer 3 (step S15), displays the measurement result display screen on the image display unit 62 (step S16), and the process ends.

Figure 16:
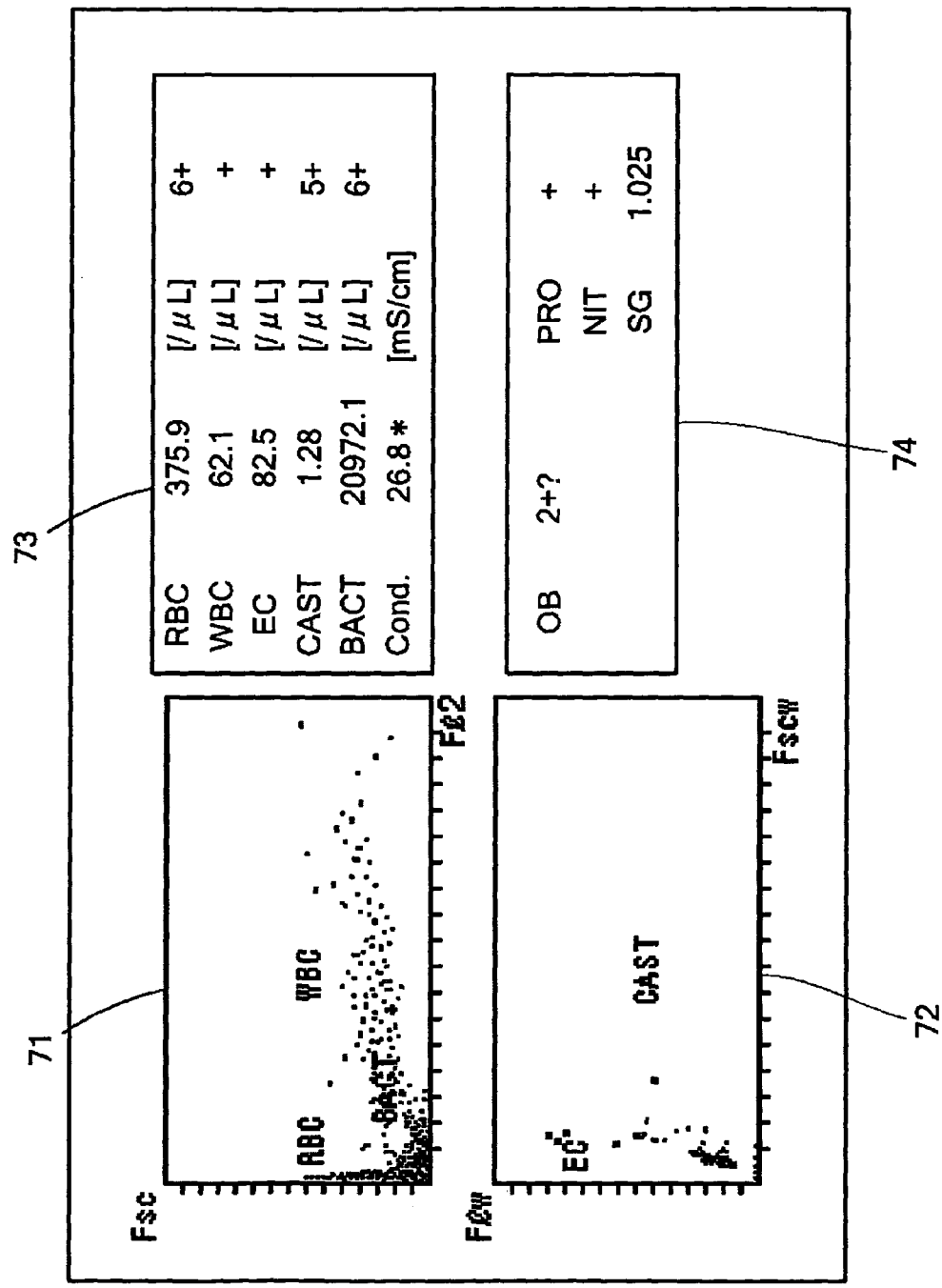
FIG. 16 is a schematic view of an example of a measurement result display screen displayed by a computer on an image display unit of the present embodiment.

FIG. 16 is a schematic view of an example of a measurement result display screen displayed by a computer 6 on an image display unit 62 of the present embodiment. As shown in FIG. 16, scattergrams and measurement values for each measurement item are displayed on the measurement result display screen. More specifically, two scattergrams 71 and 72 prepared based on the scattered light information and fluorescent light information are arranged vertically and displayed on the left-of-center area of the measurement result display screen, and measurement value display areas 73 and 74 are arranged vertically and displayed on the right-of-center area of the measurement result display screen. Among the measurement results of the urinary particle analyzer 3, the red blood cell concentration (RBC), white blood cell concentration (WBC), epithelial cell concentration (EC), cast concentration (CAST), bacteria concentration (BACT), and conductivity (COND) measurement values are displayed in the top measurement value display area 73. Among the measurement results of the urine qualitative analyzer 2, the occult blood (OB), protein concentration (PRO), nitrite concentration (NIT), and specific gravity measurement values are displayed in the bottom measurement value display area 74. Furthermore, the measurement items set in the crosscheck error tables are displayed with symbol [?] next to the measurement result to indicate low reliability data. When the low reliability flag is set for the conductivity measurement result, the symbol [*] is displayed next to the measurement result to indicate low reliability data. FIG. 16 shows a screen in which [*] is displayed next to the conductivity measurement result. In this way a user can be alerted to the low reliability of the conductivity measurement result.

The operation for setting the correlative relationships in the system for checking measurement results of the embodiment of the present invention is described below. The correlation setting operation can be divided into two main operations which include the rank setting operation and the crosscheck table setting operation. The rank setting operation is first described below.

Figure 17:
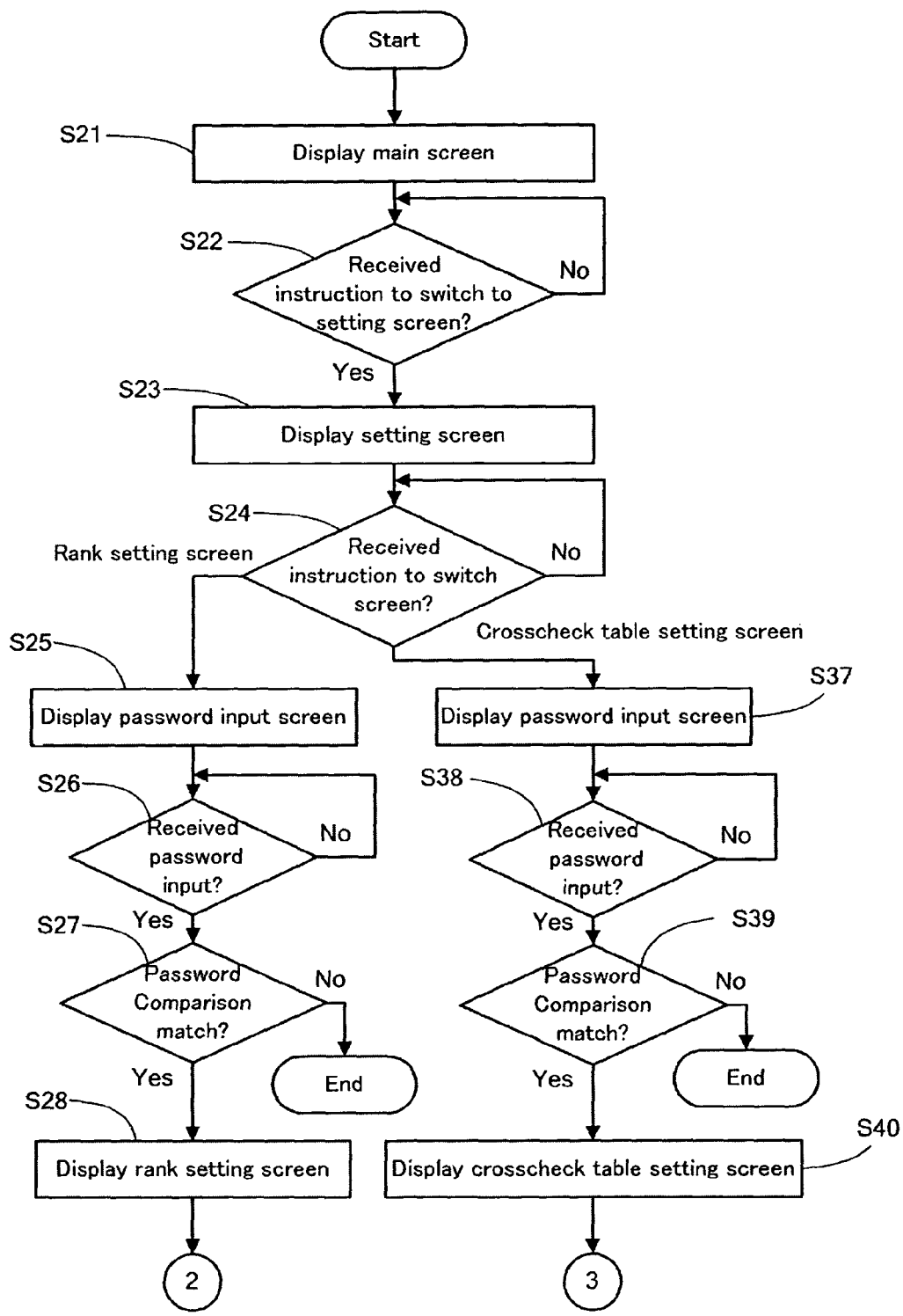
FIG. 17 is a flow chart showing the sequence of the correlative relationship setting process by the computer program of an embodiment of the present invention.
Figure 18:
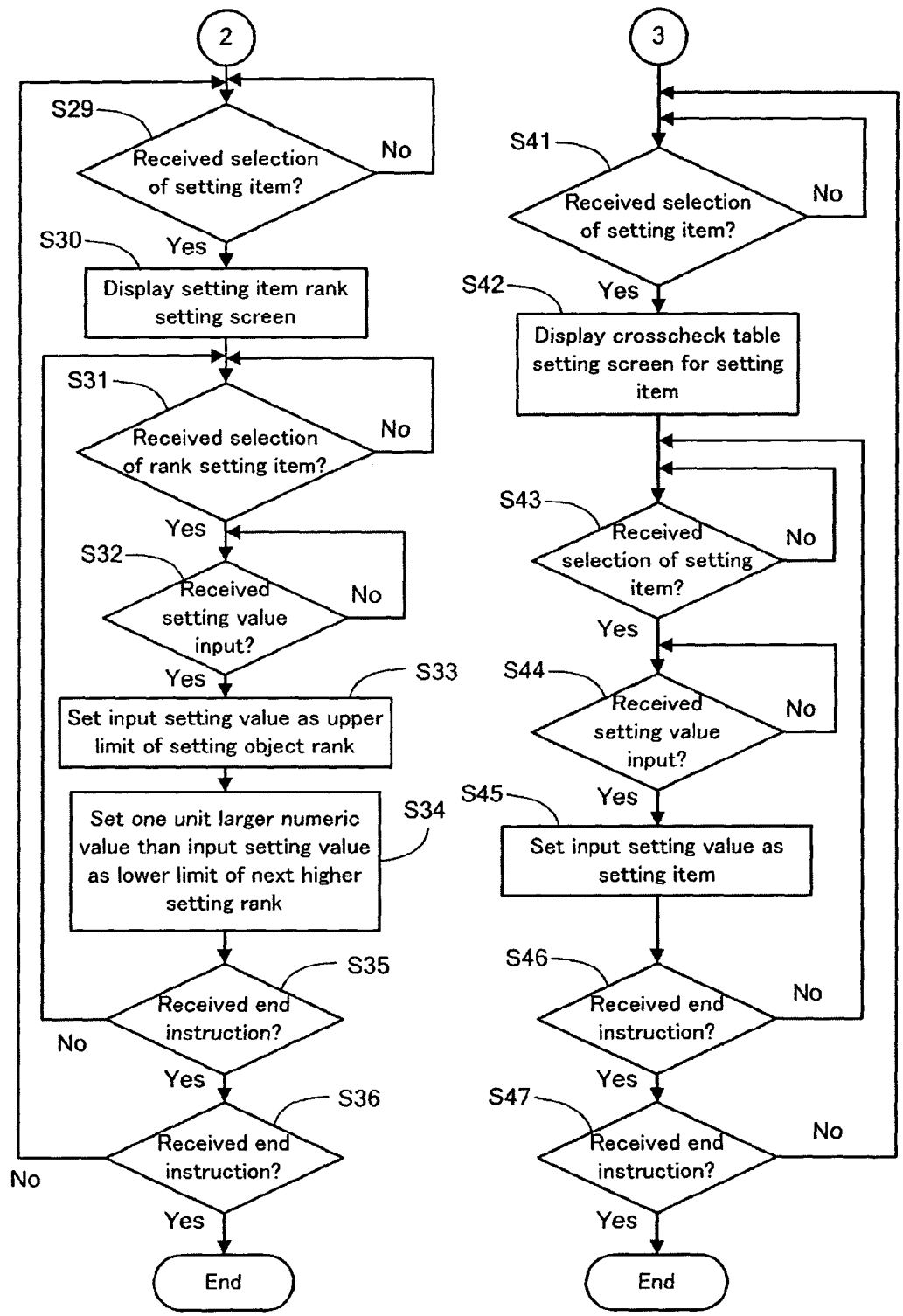
FIG. 18 is a flow chart showing the sequence of the correlative relationship setting process by the computer program of an embodiment of the present invention.

FIGS. 17 and 18 are flow charts showing the sequence of the correlation setting operation accomplished by the computer program of the embodiment of the present invention executed by the computer 6. After the computer program starts, a main screen (not shown in the drawings) is displayed on the image display unit 62 when the CPU 61a executes the computer program of the present embodiment. A software key [setting key] for invoking the setting screen for performing various setting of the computer 6 is displayed on this main screen. In the main screen, a user operates the mouse of the input unit 63 so as to move the mouse button over the [setting key] displayed the image display unit 62, and instructs the computer 6 to switch to the setting screen by pressing (clicking the left mouse button. When the instruction to switch to the setting screen has been received (step S22: YES)), the CPU 61a displays the setting screen on the image display unit 62 (step S23). In this setting screen are displayed at least two software keys, including a [rank key] and [crosscheck key] (not shown in the drawings). When the user clicks on either the rank key or crosscheck key, the computer 6 is instructed to switch the screen to either a rank setting screen or a crosscheck setting screen. When the user clicks on the rank key and the instruction to switch to the rank setting screen has been received (step S24: [rank setting screen]), the CPU 61a displays the password input screen for inputting a password on the image display unit 62 (step S25), and the user inputs a password. This step is desirable from a security standpoint so that setting and changing the set ranks of important items is only allowed by specific users (for example, a system administrator) or support personnel. When an input password from a user has been received (step S26: YES), the input password is compared to a previously recorded password (step S27), and when the passwords do not match (step S27: NO), the process ends. When the passwords match in step S27 (step S27: YES), the CPU 61a displays the rank setting screen which allows the ranks to be set (step S28).

Figure 19:
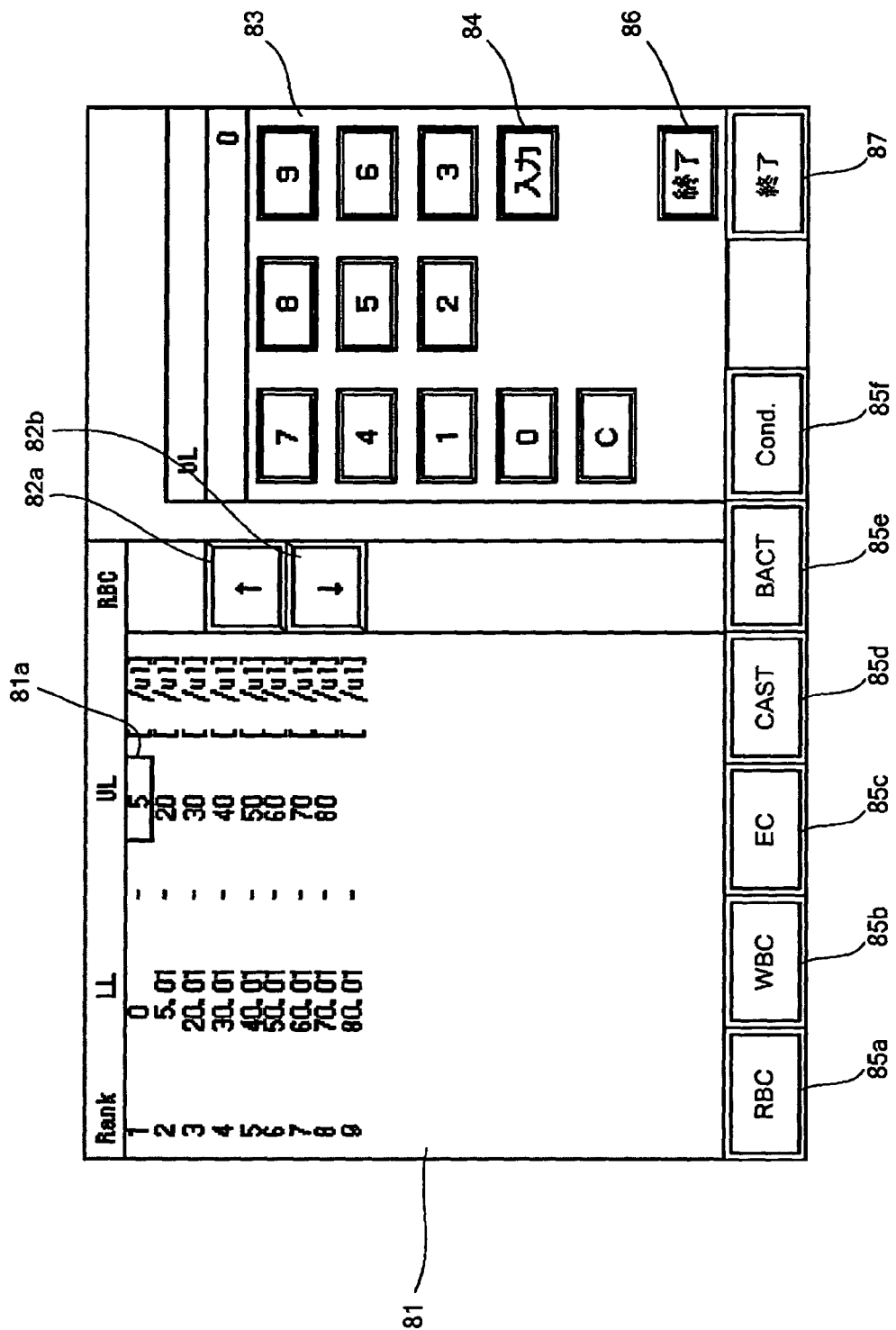
FIG. 19 is a schematic view of an example of the rank setting screen.

FIG. 19 is a schematic view of an example of the rank setting screen. As shown in FIG. 19, the rank setting screen displays a rank setting value display area 81, cursor 81a representing a rank setting value input box, cursor moving key 82a for moving the cursor 81a in vertical directions, ten-key pad 83 for numeric input, RBC key 85a, WBC key 85b, EC key 85c, CAST key 85d, BACT key 85e, and COND key 85f for respectively selecting as the rank setting object the red blood cell concentration RBC), white blood cell concentration (WBC), epithelial cell concentration (EC), cast concentration CAST), bacteria concentration (BACT), and conductivity (COND), an end key 86 for ending the rank setting of a measurement item, and an end key 87 for ending the rank setting process.

The CPU 61a waits for the user to select a rank setting object (step S29). When one setting object selection has been received (step S29: YES), the CPU 61a displays the rank setting screen for that object (step S30). For example, when a user clicks on the RBC key 85a, the red blood cell concentration rank setting screen is displayed. Then, the CPU 61a waits for the user to select the rank (step S31). The user can move the cursor and select a rank by suitably clicking on the cursor moving keys 82a and 82b. When a rank setting selection has been received (step S31: YES), the CPU 61a waits for a setting value input (step S32). The user inputs a numeric value by suitably clicking the ten-key pad 83, and sets numeric value input as the rank set value by clicking the input key 84. When the setting value input has been received (step S32: YES), the CPU 61a sets the input set value as the upper limit of the rank (step S33). Furthermore, the CPU 61a sets the lower limit of the next higher rank to a numeric value one unit greater than the set value received through input (step S34). For example, when the upper limit of a rank 1 is set at 5, lower limit of the next higher rank 2 is set at 5.01 just one unit higher than 5.

The CPU 61a then waits for instruction to end the rank setting of that rank setting item (step S35). In step S35, when the rank setting operation continues (step S35: NO), the CPU 61a returns to the process of step S31. The user then selects another rank as the setting object, and input a setting value for this rank. When the user clicks on the end key 86 in step S35 (step S35: YES), the CPU 61a waits for instructions to end the rank setting process (step S36). In step S36, when a rank setting operation continues (step S36: NO), the CPU 61a returns to the process of step S29. When the user has completed the rank settings for red blood cell concentration, the rank setting may continue for white blood cell concentration, epithelial cell concentration, cast concentration, bacteria concentration, and conductivity. When the user clicks on the end key 87 in step S36 (step S36: YES), the CPU 61a ends the process.

The crosscheck table setting operation is described below. When, in step S24, the user clicks on the crosscheck key and the CPU 61a has received instruction to switch the screen to the [crosscheck setting screen] (step S24: [crosscheck setting screen]), the CPU 61a displays the password input screen for inputting a password on the image display unit 62 (step S37), and the user inputs a password. When an input password from a user has been received (step S38: YES), the input password is compared to a previously recorded password (step S39), and when the passwords do not match (step S39: NO), the process ends. When the passwords match in step S39 (step S39: YES), the CPU 61a displays the crosscheck setting screen which allows the crosscheck table to be set (step S40).

Figure 20:
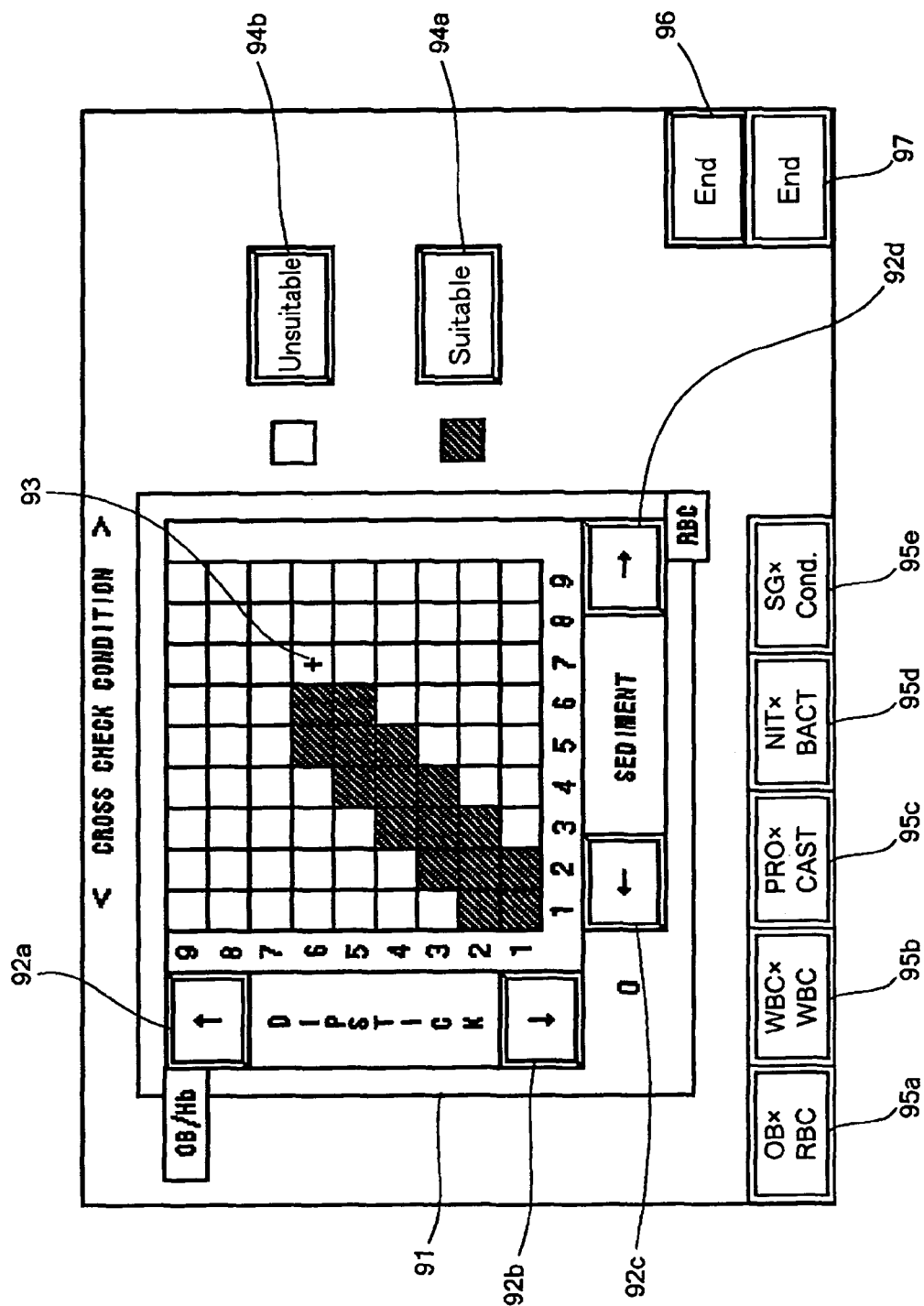
FIG. 20 is a schematic view of an example of the crosscheck table setting screen.

FIG. 20 is a schematic view of an example of the crosscheck table setting screen. As shown in FIG. 20, the crosscheck table setting screen displays a crosscheck table display area 91, cursor moving keys 92a, 02b, 92c, and 92d for moving the cursor in vertical and lateral directions, suitable key 94a and unsuitable key 94b for setting a an item selected as a setting object within the crosscheck table as a suitable region and unsuitable region, OBxRBC key 95a, WBCx-WBC key 95b, PROxCAST key 95c, NITxBACT key 95d, SGxCOND key 95e for respectively selecting occult blood OB and red blood cell concentration (RBC), white blood cell concentration (WBC) and white blood cell concentration (WBC), protein concentration (PRO) and cast concentration (CAST), nitrite concentration (NIT) and bacteria concentration (BACT), and specific gravity (SG) and conductivity (COND) as crosscheck table setting objects, end key 96 for ending item the crosscheck table setting for a selected object, and end key 97 for ending the crosscheck table setting process. Furthermore, a cursor 93 capable of moving among items within the crosscheck table is displayed in the crosscheck table display area 91.

The CPU 61a waits for the user to select a setting object in the crosscheck table (step S41). When one set of setting object selection has been received (step S41: YES), the CPU 61a displays the crosscheck table setting screen for that object (step S42). For example, when the user clicks the OBxRBC key 95a, the occult blood and red blood cell concentration crosscheck table setting screen is displayed. Then, the CPU 61a waits for the user to select the setting item (step S43). The user moves the cursor 92 by appropriately clicking the cursor moving keys 92a, 92b, 92c, and 92d to select the setting item. When a setting selection has been received (step S43: YES), the CPU 61a waits for a setting value input (step S44). The user input a setting value (suitable and unsuitable) by clicking either the suitable key 94a or unsuitable key 94b. When the setting value input has been received (step S44: YES), the CPU 61a sets the input set value for the setting item (step S45). For example, when a user clicks the suitable key 94a, that setting item is set as suitable, and the suitable region is switched on the display (hatched region in the drawing).

The CPU 61a then waits for instruction to end the crosscheck table setting for that setting item (step S46). When the crosscheck table setting operation continues in step S46 (step S46: NO), the CPU 61a returns to the process of step S43. The user then selects another item as the setting object, and inputs a setting value for this item. When the user clicks on the end key 96 in step S46 (step S46: YES), the CPU 61a waits for instruction to end the crosscheck table setting process. When the crosscheck table setting operation continues in step S47 (step S47: NO), the CPU 61a returns to the process of step S41. When the user ends the crosscheck table setting process for occult blood concentration and red blood cell concentration, the crosscheck table setting process may continue for the white blood cell concentration and white blood cell concentration, protein concentration and cast concentration, nitrite concentration and bacteria concentration, and specific gravity and conductivity. When the user clicks on the end key 97 in step S47 (step S47: YES), the CPU 61a ends the process.

In the system 1 for checking measurement results of the embodiment of the present invention having the structure described above is capable of cross checking specific gravity measurement results and conductivity measurement results of clinically significant urine with indications of renal dysfunction, and can evaluate the reliability of the specific gravity measurement results of the urine qualitative analyzer 2 and the conductivity measurement results of the urinary particle analyzer 3. Crosschecked matches of each measurement result between occult blood concentration and red blood cell concentration, between white blood cell concentration and white blood cell concentration, between protein concentration and cast concentration, and between nitrite concentration and bacteria concentration allows reliability evaluation in greater detail. This is particularly effective in analyzers which analyze samples that have a wide dispersion in component concentrations for each sample as in the case of urine than for samples that have smaller dispersion of component concentrations for each sample as in the case of blood and the like, since when measurement results are obtained that diverge greatly from a base value, it is difficult to determine whether the result is due to a malfunction of the apparatus or an abnormal sample.

The urinary particle analyzer 3 is provided with a temperature controller for controlling the temperature of the urine, such that conductivity fluctuation due to changes in temperature can be prevented because the conductivity of urine is measured while the urine is under temperature control by the temperature controller, thereby improving the reliability of the conductivity measurement results.

The present inventors further observed a strong influence of urine glucose concentration on conductivity as described above. The system 1 for checking measurement results of the present embodiment is structured so as to output a summary describing that the conductivity of the measured urine has a low reliability when the urine sugar concentration is measured and the measured sugar concentration is compared to a previously obtained threshold value and the comparison result discloses that the sugar concentration exceeds the threshold value. Therefore, in the system 1 for checking measurement results of the present embodiment, the reliability of the urine conductivity measurement results are evaluated based on urine sugar concentration.

Furthermore, in the system 1 for checking measurement results of the present embodiment, a user can adjust the correlative relationship between urine specific gravity and conductivity because the system receives an input correlative relationship between urine specific gravity and conductivity, and writes the input correlative relationship between urine specific gravity and conductivity to a memory unit.

Moreover, in the system 1 for checking measurement results of the present embodiment, a conductivity sensor 33d is provided to detect the shape of the urinary particle by a flow cytometric method, and measure the conductivity of the sample in the orifice 33e of the sheath flow cell 33c, such that the current can be controlled between electrodes 33f disposed with the orifice 33e therebetween based on the measurement result of the conductivity sensor 33d. In this way there is improved accuracy in detecting the shape of the urinary particle by the flow cytometric method, and the conductivity of the urine can be determined. The conductivity sensor for measuring urine conductivity may also be used as a shape detecting structure to detect the shape of the urinary particle, thereby simplifying the apparatus structure.

Although, in the system 1 for checking measurement results of the present embodiment described above, the urine qualitative analyzer 2 is described in terms of measuring the specific gravity by means of the refractive index of a sample, the invention is not limited to this arrangement inasmuch as specific gravity also may be measured by test paper, for example. However, a structure that measures specific gravity by refractive index is desirable from the perspective of the higher resolution obtained by measuring specific gravity by refractive index and the greater measurement accuracy compared to measuring specific gravity by test paper.

Although the system 1 for checking measurement results of the present embodiment has been described in terms of evaluating the reliability of conductivity measurement results using glucose concentration, the present invention is not limited to this arrangement inasmuch as conductivity measurement results also may be evaluated using the concentration of a sugar other than glucose, and conductivity measurement results also may be evaluated using protein concentration.

The system 1 for checking measurement results of the present embodiment has been described in terms of the urine qualitative analyzer 2 and urinary particle analyzer 3 being connected to a computer 6, the measurement results of the urine qualitative analyzer 2 and urinary particle analyzer 3 transmitted measurement results to the computer 6, and evaluating the reliability of the conductivity measurement results and crosscheck of the measurement result of each measurement result by the computer 6; however, the present invention is not limited to this arrangement inasmuch as, for example, the apparatus for checking measurement results may be provided as a function in the urinary particle analyzer 3. In this case, the urine qualitative analyzer 2 and urinary particle analyzer 3 are connected, the measurement results of the urine qualitative analyzer 2 are transmitted to the urinary particle analyzer 3, and the urinary particle analyzer 3 crosschecks the measurement results of the urinary particle analyzer 3 and the measurement results received from the urine qualitative analyzer 2. Furthermore, the display screen displayed on the image display unit 62 of the computer 6 may be displayed on a display unit such as an LCD or the like provided on the urinary particle analyzer 3. It is desirable that a touch panel type input device is provided on the display unit so that the user may input using a finger or stylus rather than input using a mouse. The urine qualitative analyzer 2 and urinary particle analyzer 3 also may be integrated, and the apparatus for checking measurement results may be provided as a function in this integrated apparatus. In this case, the measurement items of the urine qualitative analyzer 1 and measurement items of the urinary particle analyzer 3 can be measured, and the crosscheck of the measurement results and reliability evaluation of the conductivity measurement results can be accomplished within a single apparatus. In this case, also, it is desirable that a touch panel type input device is provided on the display unit so that the user may input using a finger or stylus rather than input using a mouse.

The system 1 for checking measurement results of the present embodiment has been described in terms of the urine qualitative analyzer 2 and urinary particle analyzer 3 being connected to a computer 6, the measurement results of the urine qualitative analyzer 2 and urinary particle analyzer 3 transmitted measurement results to the computer 6, and evaluating the reliability of the conductivity measurement results and crosscheck of the measurement result of each measurement result by the computer 6; however, the present invention is not limited to this arrangement inasmuch as, for example, the apparatus for checking measurement results may be provided as a function in the urinary particle analyzer 3. In this case, the urine qualitative analyzer 2 and urinary particle analyzer 3 are connected, the measurement results of the urine qualitative analyzer 2 are transmitted to the urinary particle analyzer 3, and the urinary particle analyzer 3 crosschecks the measurement results of the urinary particle analyzer 3 and the measurement results received from the urine qualitative analyzer 2. Furthermore, the display screen displayed on the image display unit 62 of the computer 6 may be displayed on a display unit such as an LCD or the like provided on the urinary particle analyzer 3. It is desirable that a touch panel type input device is provided on the display unit so that the user may input using a finger or stylus rather than input using a mouse. The urine qualitative analyzer 2 and urinary particle analyzer 3 also may be integrated, and the apparatus for checking measurement results may be provided as a function in this integrated apparatus. In this case, the measurement items of the urine qualitative analyzer 1 and measurement items of the urinary particle analyzer 3 can be measured, and the crosscheck of the measurement results and reliability evaluation of the conductivity measurement results can be accomplished within a single apparatus. In this case, also, it is desirable that a touch panel type input device is provided on the display unit so that the user may input using a finger or stylus rather than input using a mouse.

Although the system 1 for checking measurement results of the present embodiment has been described in terms of a crosscheck error flag displayed as [?], and the low reliability flag displayed as [*], the present invention is not limited to this arrangement inasmuch as, for example, the messages may be displayed in text as [crosscheck error] and [low reliability], a measurement value that sets the crosscheck error flag may be displayed in red, a measurement value that sets the low reliability flag may be displayed in blue and the like, or the crosscheck error flag and low reliability flag may be displayed by another display method.

The foregoing detailed description and accompanying drawings have been provided by way of explanation and illustration, and are not intended to limit the scope of the appended claims. Many variations in the presently preferred embodiments illustrated herein will be obvious to one of ordinary skill in the art, and remain within the scope of the appended claims and their equivalents.

The invention claimed is:

1. A method for checking reliability of a specific gravity and/or a conductivity of a urine sample measured by at least one urine analyzer, comprising computer executable steps performed by a processor of a reliability checking system to implement:
   in a memory of the reliability checking system, storing relationship data representing an acceptable range of relationship between a specific gravity and a conductivity of urine;
   measuring a specific gravity of the urine sample by the at least one urine analyzer;
   measuring a conductivity of the urine sample measured by the at least one urine analyzer; and
   determining whether a relationship of the specific gravity and the conductivity measured from the urine sample falls within the acceptable range defined by the relationship data stored in the memory in order to judge reliability of the measured specific gravity and/or conductivity of the urine sample.

2. The method of claim 1, further comprising controlling a temperature of the urine sample constant at the at least one urine analyzer while the analyzer is measuring the conductivity of the urine sample.

3. The method of claim 1, further comprising:
   measuring a sugar concentration of the urine sample by the at least one urine analyzer;
   comparing the measured sugar concentration with a predetermined threshold value; and
   indicating low reliability of the measured urine conductivity if the measured sugar concentration exceeds the threshold value.

4. A reliability checking system configured to check reliability of a specific gravity and/or a conductivity of a urine sample measured by a urine analyzer comprising:
   at least one urine analyzer configured to measure a specific gravity and a conductivity of a urine sample; and
   a CPU and a memory that stores first relationship data representing an acceptable range of relationship between a specific gravity and a conductivity of urine, wherein the memory further stores a computer program executed by the CPU to determine whether a relationship of the specific gravity and the conductivity measured from the urine sample falls within the acceptable range defined by the first relationship data stored in the memory in order to determine reliability of the measured specific gravity and/or conductivity of the urine sample.

5. The system of claim 4, wherein the at least one urine analyzer controls a temperature of the urine sample constant while measuring the conductivity of the urine sample.

6. The system of claim 4, wherein the at least one urine analyzer measures a sugar concentration of the urine sample, and the memory further stores a program executable by the CPU to:

compare the measured sugar concentration with a predetermined threshold value; and indicate low reliability of the measured urine conductivity if the measured sugar concentration exceeds the threshold value.

7. The system of claim 4, wherein the memory further stores a program executable by the CPU to receive updated relationship data and update the relationship data stored in the memory.

8. The system of claim 4, wherein the at least one urine analyzer comprises:

a flow cell provided with an orifice through which the urine sample flows;

a light-emitting element configured to emit light to the orifice; and a light-receiving element configured to receive the light coming from the light-emitting element through the orifice, wherein the at least one urine analyzer detects constituents in the urine sample passing through the orifice, based on an amount of light received by the light-receiving element.

9. The system of claim 4, wherein the at least one urine analyzer measures an occult blood concentration and a red blood cell concentration in the urine sample;

the memory stores second relationship data representing an acceptable range of relationship between an occult blood concentration and a red blood cell concentration of urine; and the memory further stores a program executable by the CPU to determine whether a relationship of the occult blood concentration and the red blood cell concentration measured from the urine sample falls within the acceptable range defined by the second relationship data in order to determine reliability of the measured occult blood concentration and/or red blood cell concentration in the urine sample.

10. The system of claim 4, wherein the system comprises more than one urine analyzers;

one of the urine analyzers measures a white blood cell concentration of the urine sample;

another of the urine analyzers measures a white blood cell concentration of the urine sample;

the memory stores third relationship data representing an acceptable range of relationship between white blood cell concentrations of urine measured by said one and another urine analyzers; and the memory further stores a program executable by the CPU to determine whether a relationship of the white blood cell concentrations measured by said one and another urine analyzers falls within the acceptable range defined by the third relationship data in order to determine reliability of the white blood cell concentrations measured by said one and another urine analyzers.

11. The system of claim 4, wherein the at least one urine analyzer measures a protein concentration and a cast concentration of the urine sample;

the memory stores fourth relationship data representing an acceptable range of relationship between a protein concentration and a cast concentration of urine; and the memory further stores a program executable by the CPU to determine whether a relationship of the measured protein concentration and cast concentration falls within the acceptable range defined by the fourth relationship data in order to determine reliability of the measured protein concentration and/or cast concentration.

12. The system of claim 4, wherein the at least one urine analyzer measures a nitrite concentration and a bacteria concentration of the urine sample;

the memory stores fifth relationship data representing an acceptable range of relationship between a nitrite concentration and a bacteria concentration of urine; and the memory further stores a program executable by the CPU to determine whether a relationship of the nitrite concentration and the bacteria concentration measured from the urine sample falls within the acceptable range defined by the fifth relationship data in order to determine reliability of the measured nitrite concentration and/or urine bacteria concentration in the urine sample.

* * * * *

UNITED STATES PATENT AND TRADEMARK OFFICE
CERTIFICATE OF CORRECTION

| | | |
|---|---|---|
| PATENT NO. | : 8,008,089 B2 | Page 1 of 1 |
| APPLICATION NO. | : 11/238896 | |
| DATED | : August 30, 2011 | |
| INVENTOR(S) | : Fukuda et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 780 days.

Signed and Sealed this
Twenty-fourth Day of January, 2012

David J. Kappos
*Director of the United States Patent and Trademark Office*